(12) United States Patent
Roslin et al.

(10) Patent No.: US 8,623,042 B2
(45) Date of Patent: Jan. 7, 2014

(54) ARTIFICIAL GASTRIC VALVE

(75) Inventors: Mitchell Steven Roslin, Armonk, NY (US); Joseph Shiloh, Haifa (IL)

(73) Assignee: Mitchell Roslin, Armonk, NY (US)

( * ) Notice: Subject to any disclaimer, the term of this patent is extended or adjusted under 35 U.S.C. 154(b) by 659 days.

(21) Appl. No.: 12/707,920

(22) Filed: Feb. 18, 2010

(65) Prior Publication Data

US 2010/0274274 A1 Oct. 28, 2010

Related U.S. Application Data

(62) Division of application No. 11/397,795, filed on Apr. 5, 2006.

(60) Provisional application No. 60/670,546, filed on Apr. 13, 2005.

(51) Int. Cl.
*A61M 29/00* (2006.01)

(52) U.S. Cl.
USPC ........................................................ 606/191

(58) Field of Classification Search
USPC ............. 606/191–192, 196, 139–158; 600/37
See application file for complete search history.

(56) References Cited

U.S. PATENT DOCUMENTS

| | | |
|---|---|---|
| 1,174,814 A | 3/1916 | Brennan et al. |
| 1,830,947 A | 11/1931 | Klingel |
| 1,999,683 A | 4/1935 | Borresen |
| 2,163,048 A | 6/1939 | McKee |
| 2,339,138 A | 1/1944 | Black |
| 2,405,667 A | 8/1946 | Ottesen |
| 2,438,231 A | 3/1948 | Schultz et al. |
| 2,635,907 A | 4/1953 | Heimbuch |
| 2,714,469 A | 8/1955 | Carlson |
| 2,936,980 A | 5/1960 | Rapata |
| 3,059,645 A | 10/1962 | Hasbrouck et al. |
| 3,189,961 A | 6/1965 | Heller |
| 3,667,081 A | 6/1972 | Burger |
| 3,840,018 A | 10/1974 | Heifetz |
| 3,955,834 A | 5/1976 | Ahlrot |
| 4,053,176 A | 10/1977 | Hilbush |
| 4,118,805 A | 10/1978 | Reimels |
| 4,133,315 A | 1/1979 | Berman et al. |
| 4,157,713 A | 6/1979 | Clarey |

(Continued)

FOREIGN PATENT DOCUMENTS

| | | |
|---|---|---|
| CA | 949965 | 6/1974 |
| CN | 1250382 | 4/2000 |

(Continued)

OTHER PUBLICATIONS

Brown et al; "Symmetrical Pouch Dilation After Laparoscopic Adjustable Gastric Banding: Incidence and Management"; Obesity Surgery; V. 18, pp. 1104-1108; 2008.

(Continued)

*Primary Examiner* — Charles A Marmor, II
*Assistant Examiner* — Catherine E Burk

(57) ABSTRACT

An apparatus and method are disclosed for treating overweight and obese patients by applying a restrictive Artificial Gastric Valve (AGV) on part of the stomach. The apparatus includes a mechanism to control the opening of the AGV automatically on demand, dynamically and progressively. The controlled opening of the AGV inside the stomach controls and regulates the flow of food.

29 Claims, 11 Drawing Sheets

(56) References Cited

U.S. PATENT DOCUMENTS

| | | |
|---|---|---|
| 4,176,412 A | 12/1979 | Peterson |
| 4,236,521 A | 12/1980 | Lauterjung |
| 4,271,827 A | 6/1981 | Angelchick |
| 4,299,012 A | 11/1981 | Oetiker |
| 4,340,083 A | 7/1982 | Cummins |
| 4,399,809 A | 8/1983 | Baro et al. |
| 4,408,597 A | 10/1983 | Tenney, Jr. et al. |
| 4,417,567 A | 11/1983 | Trick |
| 4,424,208 A | 1/1984 | Wallace et al. |
| 4,442,153 A | 4/1984 | Meltsch |
| 4,450,375 A | 5/1984 | Siegal |
| 4,485,805 A | 12/1984 | Foster, Jr. |
| 4,492,004 A | 1/1985 | Oetiker |
| 4,551,862 A | 11/1985 | Haber |
| 4,558,699 A | 12/1985 | Bashour |
| 4,559,699 A | 12/1985 | Owen et al. |
| 4,582,640 A | 4/1986 | Smestad et al. |
| 4,582,865 A | 4/1986 | Balazs et al. |
| 4,592,339 A | 6/1986 | Kuzmak et al. |
| 4,592,355 A | 6/1986 | Antebi |
| 4,601,713 A | 7/1986 | Fuqua |
| 4,667,672 A | 5/1987 | Romanowski |
| 4,671,351 A | 6/1987 | Rappe |
| 4,693,695 A | 9/1987 | Cheng |
| 4,694,827 A | 9/1987 | Weiner et al. |
| 4,696,288 A | 9/1987 | Kuzmak et al. |
| 4,708,140 A | 11/1987 | Baron |
| 4,716,154 A | 12/1987 | Malson et al. |
| 4,753,086 A | 6/1988 | Schmidt |
| 4,760,837 A | 8/1988 | Petit |
| 4,803,075 A | 2/1989 | Wallace et al. |
| 4,881,939 A | 11/1989 | Newman |
| 4,883,467 A | 11/1989 | Franetzki et al. |
| 4,886,787 A | 12/1989 | de Belder et al. |
| 4,896,787 A | 1/1990 | Delamour et al. |
| 4,915,690 A | 4/1990 | Cone et al. |
| 4,925,446 A | 5/1990 | Garay et al. |
| 4,944,487 A | 7/1990 | Holtermann |
| 4,944,659 A | 7/1990 | Labbe et al. |
| 4,958,791 A | 9/1990 | Nakamura |
| 4,969,899 A | 11/1990 | Cox, Jr. |
| 4,994,019 A | 2/1991 | Fernandez et al. |
| 5,045,060 A | 9/1991 | Melsky et al. |
| 5,074,868 A | 12/1991 | Kuzmak |
| 5,084,061 A | 1/1992 | Gau et al. |
| 5,091,171 A | 2/1992 | Yu et al. |
| 5,116,652 A | 5/1992 | Alzner |
| 5,120,313 A | 6/1992 | Elftman |
| 5,143,724 A | 9/1992 | Leshchiner et al. |
| 5,152,770 A | 10/1992 | Bengmark et al. |
| 5,160,338 A | 11/1992 | Vincent |
| 5,188,609 A | 2/1993 | Bayless et al. |
| 5,224,494 A | 7/1993 | Enhorning |
| 5,226,429 A | 7/1993 | Kuzmak |
| 5,246,456 A | 9/1993 | Wilkinson |
| 5,246,698 A | 9/1993 | Leshchiner et al. |
| 5,259,399 A | 11/1993 | Brown |
| 5,326,349 A | 7/1994 | Baraff |
| 5,343,894 A | 9/1994 | Frisch et al. |
| 5,356,883 A | 10/1994 | Kuo et al. |
| 5,360,445 A | 11/1994 | Goldowsky |
| 5,391,156 A | 2/1995 | Hildwein et al. |
| 5,399,351 A | 3/1995 | Leshchiner et al. |
| 5,449,363 A | 9/1995 | Brust et al. |
| 5,449,368 A | 9/1995 | Kuzmak |
| 5,458,568 A | 10/1995 | Racchini et al. |
| 5,509,888 A | 4/1996 | Miller |
| 5,531,716 A | 7/1996 | Luzio et al. |
| 5,535,752 A | 7/1996 | Halperin et al. |
| 5,554,113 A | 9/1996 | Novak et al. |
| 5,562,714 A | 10/1996 | Grevious |
| 5,601,604 A | 2/1997 | Vincent |
| 5,607,418 A | 3/1997 | Arzbaecher |
| 5,633,001 A | 5/1997 | Agerup |
| 5,653,718 A | 8/1997 | Yoon |
| 5,658,298 A | 8/1997 | Vincent et al. |
| 5,676,162 A | 10/1997 | Larson, Jr. et al. |
| 5,695,504 A | 12/1997 | Gifford, III et al. |
| 5,704,893 A | 1/1998 | Timm |
| 5,713,911 A | 2/1998 | Racenet et al. |
| 5,733,257 A | 3/1998 | Sternby |
| 5,748,200 A | 5/1998 | Funahashi |
| 5,766,232 A | 6/1998 | Grevious et al. |
| 5,769,877 A | 6/1998 | Barreras, Sr. |
| 5,785,295 A | 7/1998 | Tsai |
| 5,817,113 A | 10/1998 | Gifford, III et al. |
| 5,827,529 A | 10/1998 | Ono et al. |
| 5,833,698 A | 11/1998 | Hinchliffe et al. |
| 5,861,014 A | 1/1999 | Familoni |
| RE36,176 E | 3/1999 | Kuzmak |
| 5,886,042 A | 3/1999 | Yu et al. |
| 5,904,697 A | 5/1999 | Gifford, III et al. |
| 5,910,149 A | 6/1999 | Kuzmak |
| 5,928,195 A | 7/1999 | Malamud et al. |
| 5,938,669 A | 8/1999 | Klaiber et al. |
| 5,944,696 A | 8/1999 | Bayless et al. |
| 5,944,751 A | 8/1999 | Laub |
| 5,993,473 A | 11/1999 | Chan et al. |
| 6,013,679 A | 1/2000 | Kuo et al. |
| 6,024,340 A | 2/2000 | Lazarus et al. |
| 6,024,704 A | 2/2000 | Meador et al. |
| 6,048,309 A | 4/2000 | Flom et al. |
| 6,067,991 A | 5/2000 | Forsell |
| 6,074,341 A | 6/2000 | Anderson et al. |
| 6,074,378 A | 6/2000 | Mouri et al. |
| 6,083,249 A | 7/2000 | Familoni |
| 6,090,131 A | 7/2000 | Daley |
| 6,102,678 A | 8/2000 | Peclat |
| 6,102,922 A | 8/2000 | Jakobsson et al. |
| 6,171,321 B1 | 1/2001 | Gifford, III et al. |
| 6,193,734 B1 | 2/2001 | Bolduc et al. |
| 6,203,523 B1 | 3/2001 | Haller et al. |
| 6,210,345 B1 | 4/2001 | Van Brunt |
| 6,210,347 B1 | 4/2001 | Forsell |
| 6,221,024 B1 | 4/2001 | Miesel |
| 6,224,857 B1 | 5/2001 | Romeo et al. |
| 11,543 A1 | 8/2001 | Forsell |
| 6,306,088 B1 | 10/2001 | Krausman et al. |
| 6,327,503 B1 | 12/2001 | Familoni |
| 6,371,965 B2 | 4/2002 | Gifford, III et al. |
| 6,372,494 B1 | 4/2002 | Naughton et al. |
| 6,383,218 B1 | 5/2002 | Sourdile et al. |
| 6,383,219 B1 | 5/2002 | Telandro et al. |
| 6,387,105 B1 | 5/2002 | Gifford, III et al. |
| 91,395 A1 | 7/2002 | Gabbay |
| 6,417,750 B1 | 7/2002 | Sohn |
| 6,418,934 B1 | 7/2002 | Chin |
| 6,419,696 B1 | 7/2002 | Ortiz et al. |
| 6,432,040 B1 | 8/2002 | Meah |
| 6,439,539 B1 | 8/2002 | Powell |
| 6,443,957 B1 | 9/2002 | Addis |
| 6,443,965 B1 | 9/2002 | Gifford, III et al. |
| 6,450,173 B1 | 9/2002 | Forsell |
| 6,450,946 B1 | 9/2002 | Forsell |
| 6,451,034 B1 | 9/2002 | Gifford, III et al. |
| 6,453,907 B1 | 9/2002 | Forsell |
| 6,454,699 B1 * | 9/2002 | Forsell .......................... 600/30 |
| 6,454,700 B1 | 9/2002 | Forsell |
| 6,454,701 B1 | 9/2002 | Forsell |
| 6,454,785 B2 * | 9/2002 | De Hoyos Garza .......... 606/192 |
| 6,457,801 B1 | 10/2002 | Fish et al. |
| 6,460,543 B1 | 10/2002 | Forsell |
| 6,461,293 B1 | 10/2002 | Forsell |
| 6,463,935 B1 | 10/2002 | Forsell |
| 6,464,628 B1 | 10/2002 | Forsell |
| 6,470,892 B1 | 10/2002 | Forsell |
| 6,474,584 B1 | 11/2002 | Ekich |
| 6,475,136 B1 | 11/2002 | Forsell |
| 6,485,496 B1 | 11/2002 | Suyker et al. |
| 6,491,704 B2 | 12/2002 | Gifford, III et al. |
| 6,491,705 B2 | 12/2002 | Gifford, III et al. |
| 6,511,490 B2 | 1/2003 | Robert |
| 6,517,556 B1 | 2/2003 | Monassevitch |
| 6,527,701 B1 | 3/2003 | Sayet et al. |

(56) References Cited

U.S. PATENT DOCUMENTS

| | | |
|---|---|---|
| 6,547,801 B1 | 4/2003 | Dargent et al. |
| 6,565,582 B2 | 5/2003 | Gifford, III et al. |
| 6,579,301 B1 | 6/2003 | Bales et al. |
| 6,601,604 B1 | 8/2003 | Cooper |
| 6,615,084 B1 | 9/2003 | Cigaina |
| 6,627,620 B1 | 9/2003 | Nielsen |
| 6,630,486 B1 | 10/2003 | Royer |
| 6,632,239 B2 | 10/2003 | Snyder et al. |
| 6,646,628 B2 | 11/2003 | Shirochi et al. |
| 6,676,674 B1 | 1/2004 | Dudai |
| 6,685,668 B1 | 2/2004 | Cho et al. |
| 6,685,963 B1 | 2/2004 | Taupin et al. |
| 6,691,047 B1 | 2/2004 | Fredericks |
| 6,715,731 B1 | 4/2004 | Post et al. |
| 6,729,600 B2 | 5/2004 | Mattes et al. |
| 6,754,527 B2 | 6/2004 | Stroebel et al. |
| 148,034 A1 | 7/2004 | Kagan et al. |
| 6,767,924 B2 | 7/2004 | Yu et al. |
| 6,811,136 B2 | 11/2004 | Eberhardt et al. |
| 6,820,651 B2 | 11/2004 | Seuret et al. |
| 6,834,201 B2 | 12/2004 | Gillies et al. |
| 55,039 A1 | 3/2005 | Burnett et al. |
| 6,871,090 B1 | 3/2005 | He et al. |
| 6,889,086 B2 | 5/2005 | Mass et al. |
| 6,916,326 B2 | 7/2005 | Benchetrit |
| 6,921,819 B2 | 7/2005 | Piron et al. |
| 6,924,273 B2 | 8/2005 | Pierce |
| 6,940,467 B2 | 9/2005 | Fisher et al. |
| 6,966,875 B1 | 11/2005 | Longobardi |
| 7,017,583 B2 | 3/2006 | Forsell |
| 7,021,147 B1 | 4/2006 | Subramanian et al. |
| 7,037,344 B2 | 5/2006 | Kagan et al. |
| 7,040,349 B2 | 5/2006 | Moler et al. |
| 7,054,690 B2 | 5/2006 | Imran |
| 7,058,434 B2 | 6/2006 | Wang et al. |
| 7,060,080 B2 | 6/2006 | Bachmann |
| 7,066,486 B2 | 6/2006 | Birk |
| 7,118,526 B2 * | 10/2006 | Egle .................. 600/37 |
| 7,119,062 B1 | 10/2006 | Alvis et al. |
| 7,128,750 B1 | 10/2006 | Stergiopulos |
| 7,144,400 B2 | 12/2006 | Byrum et al. |
| 7,172,607 B2 | 2/2007 | Hofle et al. |
| 7,177,693 B2 | 2/2007 | Starkebsum |
| 7,191,007 B2 | 3/2007 | Desai et al. |
| 7,204,821 B1 | 4/2007 | Clare et al. |
| 7,223,239 B2 | 5/2007 | Schulze et al. |
| 7,238,191 B2 | 7/2007 | Bachmann |
| 7,240,607 B2 | 7/2007 | Fish |
| 7,255,675 B2 | 8/2007 | Gertner et al. |
| 7,263,405 B2 | 8/2007 | Boveja et al. |
| 7,282,023 B2 | 10/2007 | Frering |
| 7,288,064 B2 | 10/2007 | Boustani et al. |
| 7,297,103 B2 | 11/2007 | Jarsaillon et al. |
| 7,299,082 B2 | 11/2007 | Feldman et al. |
| 7,310,557 B2 | 12/2007 | Maschino et al. |
| 7,311,716 B2 | 12/2007 | Byrun |
| 7,311,717 B2 | 12/2007 | Egle |
| 7,314,443 B2 | 1/2008 | Jordan et al. |
| 7,314,636 B2 | 1/2008 | Caseres et al. |
| 7,338,433 B2 | 3/2008 | Coe |
| 7,340,306 B2 | 3/2008 | Barrett et al. |
| 7,351,198 B2 | 4/2008 | Byrum et al. |
| 7,351,240 B2 | 4/2008 | Hassler, Jr. et al. |
| 7,364,542 B2 | 4/2008 | Jambor et al. |
| 7,367,340 B2 | 5/2008 | Nelson et al. |
| 7,367,937 B2 | 5/2008 | Jambor et al. |
| 7,374,565 B2 | 5/2008 | Hassler, Jr. et al. |
| 7,390,294 B2 | 6/2008 | Hassler, Jr. |
| 7,396,353 B2 | 7/2008 | Lorenzen et al. |
| 7,416,528 B2 | 8/2008 | Crawford et al. |
| 7,457,668 B2 | 11/2008 | Cancel et al. |
| 7,481,763 B2 | 1/2009 | Hassler, Jr. et al. |
| 7,500,944 B2 | 3/2009 | Byrum et al. |
| 7,502,649 B2 | 3/2009 | Ben-Haim et al. |
| 7,530,943 B2 | 5/2009 | Lechner |
| 7,594,885 B2 | 9/2009 | Byrum |
| 7,599,743 B2 | 10/2009 | Hassler, Jr. et al. |
| 7,599,744 B2 | 10/2009 | Giordano et al. |
| 7,601,162 B2 | 10/2009 | Hassler, Jr. et al. |
| 7,615,001 B2 | 11/2009 | Jambor et al. |
| 7,618,365 B2 | 11/2009 | Jambor et al. |
| 7,658,196 B2 | 2/2010 | Ferreri et al. |
| 7,670,279 B2 | 3/2010 | Gertner |
| 7,699,770 B2 | 4/2010 | Hassler, Jr. et al. |
| 7,712,470 B2 | 5/2010 | Gertner |
| 7,727,141 B2 | 6/2010 | Hassler, Jr. et al. |
| 7,741,476 B2 | 6/2010 | Lebreton |
| 7,758,493 B2 | 7/2010 | Gingras |
| 7,763,039 B2 | 7/2010 | Ortiz et al. |
| 7,766,815 B2 | 8/2010 | Ortiz |
| 7,771,439 B2 | 8/2010 | Griffiths |
| 7,775,215 B2 | 8/2010 | Hassler, Jr. et al. |
| 7,775,966 B2 | 8/2010 | Dlugos et al. |
| 7,775,967 B2 | 8/2010 | Gertner |
| 7,794,386 B2 | 9/2010 | Brooks |
| 7,811,298 B2 | 10/2010 | Birk |
| 7,824,422 B2 | 11/2010 | Benchetrit |
| 7,828,813 B2 | 11/2010 | Mouton |
| 7,832,407 B2 | 11/2010 | Gertner |
| 7,841,978 B2 | 11/2010 | Gertner |
| 7,844,342 B2 | 11/2010 | Dlugos, Jr. et al. |
| 7,862,502 B2 | 1/2011 | Pool et al. |
| 7,879,068 B2 | 2/2011 | Dlugos et al. |
| 7,951,067 B2 | 5/2011 | Byrum et al. |
| 2002/0072780 A1 | 6/2002 | Foley |
| 2002/0095181 A1 | 7/2002 | Beyar |
| 2002/0098097 A1 | 7/2002 | Singh |
| 2002/0139208 A1 | 10/2002 | Yatskov |
| 2002/0183765 A1 | 12/2002 | Adams |
| 2002/0193679 A1 | 12/2002 | Malave et al. |
| 2002/0198548 A1 | 12/2002 | Robert |
| 2003/0014003 A1 | 1/2003 | Gertner |
| 2003/0019498 A1 | 1/2003 | Forsell |
| 2003/0045775 A1 | 3/2003 | Forsell |
| 2003/0045902 A1 | 3/2003 | Weadock |
| 2003/0060873 A1 | 3/2003 | Gertner et al. |
| 2003/0066536 A1 | 4/2003 | Forsell |
| 2003/0073880 A1 | 4/2003 | Polsky et al. |
| 2003/0093157 A1 | 5/2003 | Casares et al. |
| 2003/0100910 A1 | 5/2003 | Gifford, III et al. |
| 2003/0120288 A1 | 6/2003 | Benchetrit |
| 2003/0148995 A1 | 8/2003 | Piron et al. |
| 2003/0158564 A1 | 8/2003 | Benchetrit |
| 2003/0158569 A1 * | 8/2003 | Wazne .................. 606/191 |
| 2003/0181890 A1 | 9/2003 | Schulze et al. |
| 2003/0181917 A1 | 9/2003 | Gertner |
| 2003/0191433 A1 | 10/2003 | Prentiss |
| 2003/0208212 A1 | 11/2003 | Cigaina |
| 2004/0000843 A1 | 1/2004 | East |
| 2004/0044332 A1 | 3/2004 | Stergiopulos |
| 2004/0049209 A1 | 3/2004 | Benchetrit |
| 2004/0059393 A1 | 3/2004 | Policker et al. |
| 2004/0068847 A1 | 4/2004 | Belisle et al. |
| 2004/0106899 A1 | 6/2004 | McMichael et al. |
| 2004/0133219 A1 | 7/2004 | Forsell |
| 2004/0147816 A1 | 7/2004 | Policker et al. |
| 2004/0153106 A1 | 8/2004 | Dudai |
| 2004/0162595 A1 | 8/2004 | Foley |
| 2004/0215159 A1 | 10/2004 | Forsell |
| 2004/0230137 A1 | 11/2004 | Mouton |
| 2004/0254536 A1 | 12/2004 | Conlon et al. |
| 2004/0254537 A1 | 12/2004 | Conlon et al. |
| 2004/0260319 A1 | 12/2004 | Egle |
| 2004/0267288 A1 | 12/2004 | Byrum et al. |
| 2004/0267291 A1 | 12/2004 | Byrum et al. |
| 2004/0267292 A1 | 12/2004 | Byrum et al. |
| 2004/0267293 A1 | 12/2004 | Byrum et al. |
| 2004/0267377 A1 | 12/2004 | Egle |
| 2005/0002984 A1 | 1/2005 | Byrum et al. |
| 2005/0038484 A1 | 2/2005 | Knudson et al. |
| 2005/0038498 A1 | 2/2005 | Dubrow et al. |
| 2005/0070934 A1 | 3/2005 | Tanaka et al. |
| 2005/0070937 A1 | 3/2005 | Jambor et al. |
| 2005/0100779 A1 | 5/2005 | Gertner |

(56) References Cited

U.S. PATENT DOCUMENTS

| | | |
|---|---|---|
| 2005/0104457 A1 | 5/2005 | Jordan et al. |
| 2005/0119672 A1 | 6/2005 | Benchetrit |
| 2005/0119674 A1 | 6/2005 | Gingras |
| 2005/0131383 A1 | 6/2005 | Chen et al. |
| 2005/0131485 A1 | 6/2005 | Knudson et al. |
| 2005/0136122 A1 | 6/2005 | Sadozai et al. |
| 2005/0142152 A1 | 6/2005 | Leshchiner et al. |
| 2005/0143765 A1 | 6/2005 | Bachmann et al. |
| 2005/0143766 A1 | 6/2005 | Bachmann et al. |
| 2005/0154274 A1 | 7/2005 | Jarsaillon et al. |
| 2005/0171568 A1 | 8/2005 | Duffy |
| 2005/0183730 A1 | 8/2005 | Byrum |
| 2005/0192531 A1 | 9/2005 | Birk |
| 2005/0192601 A1 | 9/2005 | Demarais |
| 2005/0192629 A1 | 9/2005 | Saadat et al. |
| 2005/0216042 A1 | 9/2005 | Gertner |
| 2005/0226936 A1 | 10/2005 | Agerup |
| 2005/0228415 A1 | 10/2005 | Gertner |
| 2005/0228504 A1 | 10/2005 | Demarais |
| 2005/0240155 A1 | 10/2005 | Conlon |
| 2005/0240156 A1 | 10/2005 | Conlon |
| 2005/0240279 A1 | 10/2005 | Kagan et al. |
| 2005/0244288 A1 | 11/2005 | O'Neil |
| 2005/0250979 A1 | 11/2005 | Coe |
| 2005/0251181 A1 | 11/2005 | Bachmann |
| 2005/0251182 A1 | 11/2005 | Bachmann |
| 2005/0267406 A1 | 12/2005 | Hassler, Jr. |
| 2005/0267500 A1 | 12/2005 | Hassler, Jr. |
| 2005/0267533 A1 | 12/2005 | Gertner |
| 2005/0271729 A1 | 12/2005 | Wang |
| 2005/0277899 A1 | 12/2005 | Conlon et al. |
| 2005/0283041 A1 | 12/2005 | Egle |
| 2005/0288739 A1 | 12/2005 | Hassler, Jr. et al. |
| 2005/0288740 A1 | 12/2005 | Hassler, Jr. et al. |
| 2006/0015138 A1 | 1/2006 | Gertner |
| 2006/0020298 A1 | 1/2006 | Camilleri et al. |
| 2006/0041183 A1* | 2/2006 | Massen et al. ................ 600/16 |
| 2006/0074439 A1 | 4/2006 | Garner et al. |
| 2006/0074473 A1 | 4/2006 | Gertner |
| 2006/0089571 A1 | 4/2006 | Gertner |
| 2006/0122147 A1 | 6/2006 | Wohlrab |
| 2006/0142700 A1 | 6/2006 | Sobelman et al. |
| 2006/0142790 A1 | 6/2006 | Gertner |
| 2006/0161139 A1 | 7/2006 | Levine et al. |
| 2006/0161186 A1 | 7/2006 | Hassler, Jr. et al. |
| 2006/0167531 A1 | 7/2006 | Gertner et al. |
| 2006/0173238 A1* | 8/2006 | Starkebaum ................ 600/37 |
| 2006/0173424 A1 | 8/2006 | Conlon |
| 2006/0183967 A1 | 8/2006 | Lechner |
| 2006/0189887 A1 | 8/2006 | Hassler, Jr. et al. |
| 2006/0189888 A1 | 8/2006 | Hassler et al. |
| 2006/0189889 A1 | 8/2006 | Gertner |
| 2006/0194758 A1 | 8/2006 | Lebreton |
| 2006/0195139 A1 | 8/2006 | Gertner |
| 2006/0197412 A1 | 9/2006 | Rasmussen |
| 2006/0199997 A1 | 9/2006 | Hassler et al. |
| 2006/0211912 A1 | 9/2006 | Dlugos et al. |
| 2006/0211913 A1 | 9/2006 | Dlugos et al. |
| 2006/0211914 A1 | 9/2006 | Hassler et al. |
| 2006/0212051 A1 | 9/2006 | Snyder et al. |
| 2006/0212053 A1 | 9/2006 | Gertner |
| 2006/0235448 A1 | 10/2006 | Roslin et al. |
| 2006/0246137 A1 | 11/2006 | Hermitte et al. |
| 2006/0247721 A1 | 11/2006 | Maschino et al. |
| 2006/0247722 A1 | 11/2006 | Maschino et al. |
| 2006/0252982 A1 | 11/2006 | Hassler, Jr. |
| 2006/0252983 A1 | 11/2006 | Lembo et al. |
| 2006/0257488 A1 | 11/2006 | Hubbard |
| 2006/0264699 A1 | 11/2006 | Gertner |
| 2006/0276812 A1 | 12/2006 | Hill et al. |
| 2006/0293627 A1 | 12/2006 | Byrum et al. |
| 2007/0015954 A1 | 1/2007 | Dlugos |
| 2007/0015955 A1 | 1/2007 | Tsonton |
| 2007/0015956 A1 | 1/2007 | Crawford et al. |
| 2007/0016231 A1 | 1/2007 | Jambor et al. |
| 2007/0016262 A1* | 1/2007 | Gross et al. ................ 607/40 |
| 2007/0027356 A1 | 2/2007 | Ortiz |
| 2007/0027358 A1 | 2/2007 | Gertner et al. |
| 2007/0044655 A1 | 3/2007 | Fish |
| 2007/0077292 A1 | 4/2007 | Pinsky |
| 2007/0078476 A1* | 4/2007 | Hull et al. ................ 606/191 |
| 2007/0125826 A1 | 6/2007 | Shelton |
| 2007/0156013 A1 | 7/2007 | Birk |
| 2007/0167672 A1 | 7/2007 | Dlugos et al. |
| 2007/0167982 A1 | 7/2007 | Gertner et al. |
| 2007/0173685 A1 | 7/2007 | Jambor et al. |
| 2007/0173888 A1 | 7/2007 | Gertner et al. |
| 2007/0179335 A1 | 8/2007 | Gertner et al. |
| 2007/0185373 A1 | 8/2007 | Tsonton |
| 2007/0185462 A1 | 8/2007 | Byrum |
| 2007/0213836 A1 | 9/2007 | Paganon |
| 2007/0218083 A1 | 9/2007 | Brooks |
| 2007/0232848 A1 | 10/2007 | Forsell |
| 2007/0232849 A1 | 10/2007 | Gertner |
| 2007/0233170 A1 | 10/2007 | Gertner |
| 2007/0235083 A1 | 10/2007 | Dlugos |
| 2007/0243227 A1 | 10/2007 | Gertner |
| 2007/0250085 A1 | 10/2007 | Bachmann et al. |
| 2007/0250086 A1 | 10/2007 | Wiley et al. |
| 2007/0255335 A1 | 11/2007 | Herbert et al. |
| 2007/0255336 A1 | 11/2007 | Herbert et al. |
| 2007/0265598 A1* | 11/2007 | Karasik ................ 604/891.1 |
| 2007/0265645 A1 | 11/2007 | Birk et al. |
| 2007/0265646 A1 | 11/2007 | McCoy et al. |
| 2007/0293716 A1 | 12/2007 | Baker et al. |
| 2007/0298005 A1 | 12/2007 | Thibault |
| 2008/0009680 A1 | 1/2008 | Hassler, Jr. |
| 2008/0015406 A1 | 1/2008 | Dlugos et al. |
| 2008/0015501 A1 | 1/2008 | Gertner |
| 2008/0027269 A1 | 1/2008 | Gartner |
| 2008/0027469 A1 | 1/2008 | Bachmann |
| 2008/0071306 A1 | 3/2008 | Gertner |
| 2008/0097496 A1 | 4/2008 | Chang et al. |
| 2008/0108862 A1 | 5/2008 | Jordan et al. |
| 2008/0147002 A1 | 6/2008 | Gertner |
| 2008/0161717 A1 | 7/2008 | Gertner |
| 2008/0161875 A1 | 7/2008 | Stone |
| 2008/0167647 A1 | 7/2008 | Gertner |
| 2008/0167648 A1 | 7/2008 | Gertner |
| 2008/0172072 A1 | 7/2008 | Pool et al. |
| 2008/0188766 A1 | 8/2008 | Gertner |
| 2008/0195092 A1 | 8/2008 | Kim et al. |
| 2008/0208240 A1 | 8/2008 | Paz |
| 2008/0221598 A1 | 9/2008 | Dlugos et al. |
| 2008/0243071 A1 | 10/2008 | Quijano et al. |
| 2008/0249806 A1 | 10/2008 | Dlugos et al. |
| 2008/0250340 A1 | 10/2008 | Dlugos et al. |
| 2008/0250341 A1 | 10/2008 | Dlugos et al. |
| 2008/0255403 A1 | 10/2008 | Voegele et al. |
| 2008/0255414 A1 | 10/2008 | Voegele et al. |
| 2008/0255425 A1 | 10/2008 | Voegele et al. |
| 2008/0255459 A1 | 10/2008 | Voegele et al. |
| 2008/0255537 A1 | 10/2008 | Voegele et al. |
| 2008/0275294 A1 | 11/2008 | Gertner |
| 2008/0275295 A1 | 11/2008 | Gertner |
| 2008/0275484 A1 | 11/2008 | Gertner |
| 2008/0281347 A1 | 11/2008 | Gertner |
| 2008/0287969 A1 | 11/2008 | Tsonton et al. |
| 2008/0287974 A1 | 11/2008 | Widenhouse et al. |
| 2008/0287976 A1 | 11/2008 | Weaner et al. |
| 2008/0300618 A1 | 12/2008 | Gertner |
| 2008/0319435 A1 | 12/2008 | Rioux et al. |
| 2009/0054914 A1 | 2/2009 | Lechner |
| 2009/0062825 A1 | 3/2009 | Pool et al. |
| 2009/0062826 A1 | 3/2009 | Steffen |
| 2009/0082793 A1 | 3/2009 | Birk |
| 2009/0118572 A1 | 5/2009 | Lechner |
| 2009/0149874 A1 | 6/2009 | Ortiz et al. |
| 2009/0157106 A1 | 6/2009 | Marcotte et al. |
| 2009/0157107 A1 | 6/2009 | Kierath et al. |
| 2009/0157113 A1 | 6/2009 | Marcotte et al. |
| 2009/0171375 A1 | 7/2009 | Coe et al. |
| 2009/0171378 A1 | 7/2009 | Coe et al. |
| 2009/0171379 A1 | 7/2009 | Coe et al. |

(56) References Cited

U.S. PATENT DOCUMENTS

| | | | |
|---|---|---|---|
| 2009/0187202 | A1 | 7/2009 | Ortiz et al. |
| 2009/0192404 | A1 | 7/2009 | Ortiz et al. |
| 2009/0192415 | A1 | 7/2009 | Ortiz et al. |
| 2009/0192533 | A1 | 7/2009 | Dlugos, Jr. et al. |
| 2009/0192534 | A1 | 7/2009 | Ortiz et al. |
| 2009/0192541 | A1 | 7/2009 | Ortiz et al. |
| 2009/0198261 | A1 | 8/2009 | Schweikert |
| 2009/0202387 | A1 | 8/2009 | Dlugos, Jr. et al. |
| 2009/0204131 | A1 | 8/2009 | Ortiz et al. |
| 2009/0204132 | A1 | 8/2009 | Ortiz et al. |
| 2009/0209995 | A1 | 8/2009 | Byrum et al. |
| 2009/0216255 | A1 | 8/2009 | Coe et al. |
| 2009/0220176 | A1 | 9/2009 | Fusco |
| 2009/0222031 | A1 | 9/2009 | Axelsson |
| 2009/0222065 | A1 | 9/2009 | Dlugos, Jr. et al. |
| 2009/0228063 | A1 | 9/2009 | Dlugos, Jr. et al. |
| 2009/0228072 | A1 | 9/2009 | Coe et al. |
| 2009/0270904 | A1 | 10/2009 | Birk et al. |
| 2009/0306462 | A1 | 12/2009 | Lechner |
| 2010/0010291 | A1 | 1/2010 | Birk et al. |
| 2010/0049224 | A1 | 2/2010 | Vargas |
| 2010/0087843 | A1 | 4/2010 | Bertolote et al. |
| 2010/0099945 | A1 | 4/2010 | Birk et al. |
| 2010/0100079 | A1 | 4/2010 | Berkcan |
| 2010/0145378 | A1 | 6/2010 | Gertner |
| 2010/0152532 | A1 | 6/2010 | Marcotte |
| 2010/0168508 | A1 | 7/2010 | Gertner |
| 2010/0185049 | A1 | 7/2010 | Birk et al. |
| 2010/0191265 | A1 | 7/2010 | Lau et al. |
| 2010/0191271 | A1 | 7/2010 | Lau et al. |
| 2010/0204647 | A1 | 8/2010 | Gertner |
| 2010/0204723 | A1 | 8/2010 | Gertner |
| 2010/0217071 | A1 | 8/2010 | Ricol |
| 2010/0226988 | A1 | 9/2010 | Lebreton |
| 2010/0228080 | A1 | 9/2010 | Tavori et al. |
| 2010/0234682 | A1 | 9/2010 | Gertner |
| 2010/0249803 | A1 | 9/2010 | Griffiths |
| 2010/0280310 | A1 | 11/2010 | Raven |
| 2010/0305397 | A1 | 12/2010 | Birk et al. |
| 2010/0312046 | A1 | 12/2010 | Lau et al. |
| 2010/0312147 | A1 | 12/2010 | Gertner |
| 2010/0324358 | A1 | 12/2010 | Birk et al. |
| 2010/0324359 | A1 | 12/2010 | Birk |
| 2011/0201874 | A1 | 8/2011 | Birk et al. |

FOREIGN PATENT DOCUMENTS

| | | |
|---|---|---|
| CN | 1367670 | 9/2002 |
| DE | 4225524 | 2/1994 |
| DE | 10020688 | 12/2000 |
| EP | 0119596 | 9/1984 |
| EP | 0230747 | 8/1987 |
| EP | 0416250 | 3/1991 |
| EP | 0 611 561 A1 | 3/1994 |
| EP | 0695558 | 2/1996 |
| EP | 0 876 808 A1 | 11/1998 |
| EP | 0 876 808 B1 | 11/1998 |
| EP | 1036545 | 9/2000 |
| EP | 1 072 282 A1 | 1/2001 |
| EP | 1105073 | 6/2001 |
| EP | 1 396 242 A1 | 3/2004 |
| EP | 1 396 243 A1 | 3/2004 |
| EP | 1 491 167 A1 | 12/2004 |
| EP | 1491168 | 12/2004 |
| EP | 1529502 | 5/2005 |
| EP | 1547549 | 6/2005 |
| EP | 1574189 | 9/2005 |
| EP | 1600183 | 11/2005 |
| EP | 1602346 | 12/2005 |
| EP | 1704833 | 9/2006 |
| EP | 1719480 | 11/2006 |
| EP | 1736123 | 12/2006 |
| EP | 1736195 | 12/2006 |
| EP | 1736202 | 12/2006 |
| EP | 1743605 | 1/2007 |
| EP | 1829504 | 9/2007 |
| EP | 1829505 | 9/2007 |
| EP | 1829506 | 9/2007 |
| EP | 1967168 | 9/2008 |
| EP | 1992315 | 11/2008 |
| EP | 2074970 | 7/2009 |
| EP | 2074971 | 7/2009 |
| EP | 2074972 | 7/2009 |
| EP | 2095796 | 9/2009 |
| EP | 2095798 | 9/2009 |
| EP | 2191796 | 6/2010 |
| FR | 1566202 | 5/1969 |
| FR | 2688693 | 9/1993 |
| FR | 2769491 | 4/1999 |
| FR | 2783153 | 3/2000 |
| FR | 2797181 | 2/2001 |
| FR | 2799118 | 4/2001 |
| FR | 2823663 | 10/2002 |
| FR | 2855744 | 12/2004 |
| FR | 2921822 | 4/2009 |
| GB | 1174814 | 12/1969 |
| GB | 2090747 | 7/1982 |
| JP | 57-171676 | 10/1982 |
| JP | 1-67309 | 4/1989 |
| JP | 2-019147 | 1/1990 |
| JP | 2-132104 | 11/1990 |
| JP | 3-105702 | 11/1991 |
| JP | 11-244395 | 9/1999 |
| JP | 2003-526410 | 9/2003 |
| JP | 2005-131380 | 5/2005 |
| JP | 2005-334658 | 12/2005 |
| SE | 8503144 | 12/1986 |
| WO | WO 86/00079 | 1/1986 |
| WO | WO 86/00912 | 2/1986 |
| WO | WO 89/11701 | 11/1989 |
| WO | WO 90/00369 | 1/1990 |
| WO | WO 92/20349 | 11/1992 |
| WO | WO 94/02517 | 2/1994 |
| WO | WO 96/33751 | 1/1996 |
| WO | WO 98/35639 | 8/1998 |
| WO | WO 98/35640 | 8/1998 |
| WO | WO 00/00108 | 1/2000 |
| WO | WO 00/01428 | 1/2000 |
| WO | WO 00/09047 | 2/2000 |
| WO | WO 00/09049 | 2/2000 |
| WO | WO 00/15158 | 3/2000 |
| WO | WO 00/66196 | 11/2000 |
| WO | WO 01/10359 | 2/2001 |
| WO | WO 01/12078 | 2/2001 |
| WO | WO 01/41671 | 6/2001 |
| WO | WO 01/47435 | 7/2001 |
| WO | WO 01/47575 | 7/2001 |
| WO | WO 01/49245 | 7/2001 |
| WO | WO 01/52777 | 7/2001 |
| WO | WO 01/68007 | 9/2001 |
| WO | WO 01/85071 | 11/2001 |
| WO | WO 02/05753 | 1/2002 |
| WO | WO 02/09792 | 2/2002 |
| WO | WO 02/19953 | 3/2002 |
| WO | WO 02/053093 A2 | 7/2002 |
| WO | WO 02/065948 A1 | 8/2002 |
| WO | WO 02/096326 | 12/2002 |
| WO | WO 03/007782 | 1/2003 |
| WO | WO 02/26317 A1 | 4/2003 |
| WO | WO 03/055420 | 7/2003 |
| WO | WO 03/057092 | 7/2003 |
| WO | WO 03/059215 | 7/2003 |
| WO | WO 03/077191 A1 | 9/2003 |
| WO | WO 03/101352 | 12/2003 |
| WO | WO 03/105732 | 12/2003 |
| WO | WO 2004/014245 A1 | 2/2004 |
| WO | WO 2004/019671 | 3/2004 |
| WO | WO 2004/108025 | 12/2004 |
| WO | WO 2004/112563 | 12/2004 |
| WO | WO 2005007232 A2 * | 1/2005 |
| WO | WO 2005/009305 | 2/2005 |
| WO | WO 2005/067994 | 7/2005 |
| WO | WO 2005/072195 | 8/2005 |

(56) References Cited

FOREIGN PATENT DOCUMENTS

| WO | WO 2005/087147 | 9/2005 |
|---|---|---|
| WO | WO 2005/094447 A2 | 10/2005 |
| WO | WO 2005/112888 | 12/2005 |
| WO | WO 2006/040647 | 4/2006 |
| WO | WO 2006/049725 | 5/2006 |
| WO | WO 2006/083885 | 8/2006 |
| WO | WO 2006/108203 | 10/2006 |
| WO | WO 2007/067206 | 6/2007 |
| WO | WO 2007/081304 | 7/2007 |
| WO | WO 2007/106727 | 9/2007 |
| WO | WO 2007/114905 | 10/2007 |
| WO | WO 2007/145638 | 12/2007 |
| WO | WO 2008/063673 | 5/2008 |
| WO | WO 2008/134755 | 11/2008 |
| WO | WO 2009/050709 | 4/2009 |
| WO | WO 2009/132127 | 10/2009 |
| WO | WO 2009/136126 | 11/2009 |
| WO | WO 2010/042493 | 4/2010 |

OTHER PUBLICATIONS

Ceelen et al.; "Surgical Treatment of Severe Obesity With a Low-Pressure Adjustable Gastric Band: Experimental Data and Clinical Results in 625 Patients"; Annals of Surgery; V. 237, No. 1; pp. 10-16; 2003.
Dixon et al.; "Pregnancy After Lap-Band Surgery: Management of the Band to Achieve Healthy Weight Outcomes"; Obesity Surgery; V. 11, pp. 59-65; 2001.
Neary et al.; "Peptide YY(3-36) and Glucagon-Like Peptide-1$_{(7-36)}$ Inhibit Food Intake Additively"; Endocrinology; V.146; pp. 5120-5127; 2005.
Padidela et al.; "Elevated basal and post-feed glucagon-like petide 1 (GLP-1) concentrations in the neonatel period"; European Journal of Endocrinology; v. 160; pp. 53-58; 2009.
Shi et al.; "Sexually Dimorphic Responses to Fat Loss After Caloric Restriction or Surgical Lipectomy"; Am. J. Physiol. Endocrinol. Metab.; V. 293; E316-E326; 2007.
Xanthakos et al.; "Bariatric Surgery for Extreme Adolescent Obesity: Indications, Outcomes, and Physiologic Effects on the Gut-Brain Axis"; Pathophysiology; V. 15; pp. 135-146; 2008.
Antonio F. Corno et al., "A new implantable device for telemetric control of pulmonary blood flow," New ideas; received Apr. 24, 2004; received in revised form Jul. 12, 2002; accepted Jul. 22, 2002.
Corno, A.F., et al.; "FloWatchTM in clipped and inclipped position," Interact Cardio Vase Thorac Surg 2002; 1:46-49; Copyright @2002 The European Association for Cardio—thoracic Surgery (1 page).
Acuna-Goycolea et al.; "Mechanism of Neuropeptide Y, Peptide YY, and Pancreatic Polypeptide Inhibition of Identified Green Fluorescent Protein-Expressing GABA Neurons in the Hypothalamic Neuroendocrine Acruate Nucleus"; The Journal of Neuroscience; V. 25(32); pp. 7406-7419; Aug. 10, 2005.
Adrian et al.; "Mechanism of Pancreatic Polypeptide Release in Man." The Lancet; pp. 161-163; Jan. 22, 1977.
Anson; "Shape Memory Alloys—Medical Applications," Source: Materials World, vol. 7, No. 12, pp. 745-747, Dec. 1999.
Asakawa et al; "Antagonism of Ghrelin Receptor Reduces Food Intake and Body Weight Gain in Mice"; Gut.; V.52; pp. 947-952; 2003.
Baggio et al. "Biology of Incretins: GLP-1 and GIP"; Gastroenrology; V. 132; pp. 2131-2157; 2007.
Ballantyne; "Peptide YY(1-36) and Peptide YY(3-36): Part I. Distribution, Release, and Actions"; Obesity Surgery; V.16; pp. 651-658; 2006.
Ballantyne; "Peptide YY(1-36) and Peptide YY(3-36): Part II. Changes after Gastrointestinal Surgery and Bariatric Surgery"; Obesity Surgery; V.16; pp. 795-803; 2006.
Berne et al; "Physiology"; V. 5; pp. 55-57, 210, 428, 540, 554, 579, 584, 591; 2004.
BioEnterics Lap-Band Adjustable Gastric Banding System, Inamed Health, pub., pp. 1-115; Aug. 28, 2003.

Boulant et al.; "Cholecystokinin in Transient Lower Oesophageal Sphincter Relaxation Due to Gastric Distension in Humans"; Gut.; V. 40; pp. 575-581; 1997.
Bradjewin et al.; "Dose Ranging Study of the Effects of Cholecystokinin in Healthy Volunteers"; J. Psychiatr. Neurosci.; V. 16 (2); pp. 91-95; 1991.
Burdyga et al.; "Cholecystokinin Regulates Expression of Y2 Receptors in Vagal Afferent Neurons Serving the Stomach"; The Journal of Neuroscience; V. 28; No. 45; pp. 11583-11592; Nov. 5, 2008.
Chaptini et al.; "Neuroendocrine Regulation of Food Intake"; Current Opinion in Gastroenterology; V. 24; pp. 223-229; 2008.
Chaudhri; "Can Gut Hormones Control Appetite and Prevent Obesity?" Diabetes Care; V. 31; Supp 2; pp. S284-S289; Feb. 2008.
Cohen et al.; "Oxyntomodulin Suppresses Appetite and Reduces Food Intake in Humans"; J. Clin. Endocrinol. Metab.; V. 88; No. 10; pp. 4696-4701; 2003.
Corno et al.; "A new implantable device for telemetric control of pulmonary blood flow"; New ideas; received Apr. 24, 2004; received in revised form Jul. 12, 2002; 10 pages.
Corno et al.; "FlowWatchTM in clipped and inclipped position"; Interact Cardio Vase Thorac Surg 2002; 1:46-49; Copyright @ 2002 The European Association for Cardio-thoracic Surgery; 1 page.
Cummings et al.; "Plasma Ghrelin Levels After Diet-Induced Weight Loss or Gastric Bypass Sugery"; N. Engl J. Med; V. 346, No. 21; pp. 1623-1630; May 23, 2002.
Cummings; "Gastrointestinal Regulation of Foot Intake"; The Food Journal of Clinical Investigation; V. 117, N. 1; pp. 13-23; Jan. 2007.
Dakin et al.; "Oxyntomodulin Inhibits Food Intake in the Rat"; Endocrinology; V. 142; No. 10; pp. 4244-4250; 2001.
Dakin et al.; "Peripheral Oxyntomodulin Reduces Food Intake and Body Weight gain in Rats"; Endocrinology; V. 145; No. 6; pp. 2687-2695; Jun. 2004.
Davison; "Activation of Vagal-Gastric Mechanoreceptors by Cholecystokinin"; Proc. West. Pharmocol. Soc.; V. 29; pp. 363-366; 1986.
De Waele et al.; "Endoscopic Volume Adjustment of Intragastric Balloons for Intolerance"; Obesity Surgery; V. 11; pp. 223-224; 2001.
De Waele et al.; "Intragastric Balloons for Preoperative Weight Reduction"; Obesity Surgery; V. 58; pp. 58-60; 2001.
Desai et al.; "Molecular Weight of Heparin Using 13C Nuclear Magnetic Resonance Spectroscopy" Journal of Pharmaceutical Science, V. 84, I 2; 1995, Abstract only.
Doldi et al.; "Intragastric Balloon: Another Option for Treatment of Obesity and Morbid Obesity"; Hepato-Gastroenterology; V. 51, N. 55; pp. 294-307; Jan.-Feb. 2004.
Doldi et al.; "Treatment of Morbid Obesity with Intragastric Balloon in Association with Diet"; Obesity Surgery; V. 10, pp. 583-587; 2000.
Doldi et al; "Intragastric Balloon in Obese Patients"; Obesity Surgery; V. 10, 578-581; 2000.
Ekblad et al.; "Distribution of Pancreatic Peptide and Peptide-YY"; Peptides; V. 23; pp. 251-261; 2002.
El Khoury et al.; "Variation in Postprandial Ghrelin Status Following Ingestion of High-Carbohydrate, High Fat, and High Protein Meals in Males"; Ann Nutr Metab; V. 50; pp. 260-269; 2006.
Galloro et al; "Preliminary Endoscopic Technical Report of an New Silicone Intragastric Balloon in the Treatment of Morbid Obesity"; Obesity Surgery; V. 9, pp. 68-71; 1999.
GinShiCel MH Hydroxy Propyl Methyl Cellulose, Web Page http://www.ginshicel.cn/MHPC.html, Nov. 12, 2008.
Girard; "The incretins: From the concept to their use in the treatment of type 2 diabetes. Part A: Incretins: Concept and physiological functions"; Diabetes and Metabolism; V. 34; pp. 550-559; 2008.
Greenough et al.; "Untangling the Effects of Hunger, Anxiety, and Nausea on Energy Intake During Intravenous Cholecystokinin Octapeptide (CCK-8) Infusion"; Physiology & Behavior; V. 65, No. 2; pp. 303-310; 1998.
Grise et al.; "Peptide YY Inhibits Growth of Human Breast Cancer in Vitro and in Vivo"; Journal of Surgical Research; V. 82; pp. 151-155; 1999.
Grundy; "Signaling the State of the Digestive Tract"; Autonomic Neuroscience: Basic and Clinical; V. 125; pp. 76-80; 2006.

(56) References Cited

OTHER PUBLICATIONS

Grundy; "Vagal Control of Gastrointestinal Function"; Bailliere's Clinical Gastroenterology; V. 2; No. 1; pp. 23-43; 1988.

Hallden et al. "Evidence for a Role of the Gut Hormone PYY in the Regulation of Intestinal Fatty Acid Binding Protein Transcripts in Differentiated Subpopulations of Intestinal Epithelial Cell Hybrids"; Journal of Biological Chemistry; V. 272 (19); pp. 125916-126000; 1997.

Hameed et al.; "Gut hormones and appetite control." Oral Diseases; V. 15; pp. 18-26; 2009.

Hassan et al.; "Effects of Adjuvants to Local Anesthetics on Their Duration III Experimental Studies of Hyaluronic Acid" Abstract Pub Med [Acta Anesthesiol Scand.; 29 (4): 384-8], 1 page; May 1985.

Hodson et al.; "Management of Obesity with the New Intragastric Balloon"; Obesity Surgery; V. 11, pp. 327-329, 2001.

Holzer; "Gastrointestinal Afferents as Targets of Novel Drugs for the Treatment of Functional Bowel Disorders and Visceral Pain"; European Journal of Pharmacology; V. 429; pp. 177-193; 2001.

Houpt; "Gastrointestinal Factors in Hunger and Satiety." Neuroscience and Behavioral Reviews; V. 6; pp. 145-164; 1982.

Jones; "Molecular, pharmacological, and clinical aspects of liraglutide, a oncedaily human GLP-1 analogue"; Molecular and Cellular Endocrinology; V. 297; pp. 137-140; 2009.

Kerem et al.; "Exogenous Ghrelin Enhances Endocrine and Exocrine Regeneration in Pancreatectomized Rats"; J Gastrointest Surg.; V.13; pp. 775-783, 2009.

Kesty et al.; "Hormone-based therapies in the regulation of fuel metabolism and body weight"; Expert Opin. Biol. Ther.; V. 8; No. 11; pp. 1733-1747; 2008.

Kissileff et al.; "Peptides that Regulate Food Intake: Cholecystokinin and Stomach Distension Combine to Reduce Food Intake in Humans"; Am. J. Physiol. Regul. Integr. Comp. Physiol; V. 285; pp. 992-998; 2003.

Kojima et al.; "A role for pancreatic polypeptide in feeding and body weight regulation." Peptides; V. 28; pp. 459-463; 2007.

Kulicke et al. "Visco-Elastic Propeerties of Sodium Hyaluronate Solutions," American Institute of Physics; pp. 585-587; 2008.

Lap-Band AP System Adjustable Gastric Banding System With OmniformTM Design: Directions for Use (DFU); Allergan, 16 pages; 2009.

Le Roux et al.; "Gut Hormone Profiles Following Bariatric Surgery Favor an Anorectic State, Facilitate Weight Loss, and Improve Metabolic Parameters"; Ann. Surg; V. 243; No. 1; pp. 108-114; Jan. 2006.

Liu et al.; "Adjuvant Hormonal Treatment With Peptide YY or Its Analog Decreases Human Pancreatic Carcinoma Growth"; The American Journal of Surgery; V. 171; pp. 192-196; Jan. 1996.

Mathus-Vliegen et al. "Intragastric Balloons for Morbid Obesity: Results, Patient Tolerance and Balloon Life Span"; Br. J. Surg.; V. 77, No. 7, pp. 76-79; Jan. 1990.

Mathus-Vliegen et al. "Treating Morbid and Supermorbid Obesity" International Journal of Gastroenterology; V. 5, No. 1, pp. 9-12; 2000.

Medeiros et al.; "Processing and metabolism of Peptide-YY: Pivotal roles of Dipeptidase-IV, Aminopeptidase-P, and Endopeptidase-24. 11"; Endocrinology; V. 134, No. 5; pp. 2088-2094; 1994.

Naslund et al. "Pranidal subcutaneous injections of glucagon-like peptide-1 cause weight loss in obese human subjects"; British Journal of Nutrition; V. 91; pp. 439-446; 2004.

Potier et al.; "Protein, amino acids, and the control of food intake"; Current Opinion in Clinical Nutrition and Metabolic Care; V. 12; pp. 54-58; 2009.

Qjan et al.; "Pulmonary delivery of a GLP-1 receptor agonist, BMS-686117"; International Journal of Pharmaceutics; V. 366; pp. 218-220; 2008.

Rang et al.; "Pharmacology"; V. 5; pp. 203, 397, 402, 524; 2004.

Raybould et al.; "Integration of Postprandial Gastrointestinal Tract: Role of CCK and Sensory Pathways"; Annals of New York Academy of Science; pp. 143-156; 1994.

Renshaw et al. "Peptide YY: A Potential Therapy for Obesity"; Current Drug Targets; V. 6; pp. 171-179; 2005.

Sannino et al.; "Crosslinking of Cellulose Derivatives and Hyaluronic Acid with Water-Soluble Carbodiimide" Polymer 46; pp. 11206-11212; 2005.

Shechter et al.; "Reversible PEGylation of peptide YY3-36 prolongs its inhibition of food intake in mice"; FEBS Letters; V. 579; pp. 2439-2444; 2005.

Silver et al.; "Physical Properties of Hyaluronic Acid and Hydroxypropylmethylcellulose in Solution: Evaluation of Coating Abillity" Journal of Applied Biomaterials, V. 5; pp. 89-98, 1994.

Small et al.; "Gut hormones and the control of appetite"; TRENDS in Endocrinology and Metabolism; V. 15. No. 6; pp. 259-263; Aug. 2004.

Stanley et al.; "Gastrointestinal Satiety Signals III. Glucagon-like Peptide 1, oxyntomodulin, peptide YY, and pancreatic polypeptide"; Am. J. Physiol Gastrointest Liver Physiol; V. 286; pp. 693-697; 2004.

Tezel; "The Science of Hyaluronic Acid Dermal Fillers," Journal of Cosmetic and Laser Therapy (2008) 10: pp. 35-42.

Tolhurst et al.; "Nutritional regulation of glucagon-like peptide1 secretion"; J. Physiol.; V. 587, No. 1; pp. 27-32; 2009.

Totte et al.; "Weight Reduction by Means of Intragastric Device: Experience with the Bioenterics Intragastric Balloon"; Obesity Surgery; V. 11, pp. 519-523; 2001.

Tough et al.; "Y4 Receptors Mediate the Inhibitory Responses of Pancreatic Polypeptide in Human and Mouse Colon Mucosa"; The Journal of Pharmacology and Experimental Therapeutics; V. 319, No. 1; pp. 20-30; 2006.

Tseng et al; "Peptide YY and cancer: Current findings and potential clinical applications"; Peptides; V. 23; pp. 389-395; 2002.

Valassi et al.; "Neuroendocrine control of food intake"; Nut. Metab. & Cariovasc. Disease; V. 18; pp. 158-168; 2008.

Van Der Lely et al.; "Biological, Physiological, Pathophysiological Aspects of Ghrelin"; Endocrine Reviews; V. 25, No. 3; pp. 426-457; 2004.

Verdich et al. "A Meta-Analysis of the Effect of Glucagon-Like-Peptide-1 (7-36) Amide on ad Libitum Energy Intake in Humans"; J. Clin. Endocrinal. Metab. V. 86; pp. 4382-4389; Sep. 2001.

Wahlen et al.; "The BioEnterics Intragastric Balloon (BIB): How to Use It"; Obesity Surgery; V. 11; pp. 524-527; 2001.

Wang et al.; "Plasma Ghrelin Modulation in Gastric Band Operation and Sleeve Gastrectomy"; Obes. Surg.; pp. 357-362; 2008.

Weiner et al.; "Preparation of Extremely Obese Patients for Laparoscopic Gastric Banding by Gastric Balloon Therapy"; Obesity Surgery; V. 9, pp. 261-264, 1999.

Wynne et al.; "Subcutaneous Oxyntomodulin Reduces Body Weight in Overweight and Obese Subjects: A Double-Blind Randomized, Controlled Trial"; Diabetes; V. 54; pp. 2390-2395; 2005.

Yuzuriha et al.; "Gastrointestinal Hormones (anorexigenic peptide YY and orexigenic ghrelin) influence neural tube development"; FASEB J.; V. 21; pp. 2108-2112; 2007.

* cited by examiner

ARTIFICIAL GASTRIC VALVE

CROSS REFERENCE

This application is a divisional of application Ser. No. 11/397,795, filed Apr. 5, 2006, and this application claims the benefit under Title 35, U.S.C. §119 (e) of U.S. provisional application 60/670,546 filed on Apr. 13, 2005, the entire contents of which applications are hereby incorporated by reference.

BACKGROUND OF THE INVENTION

1. Field of the Invention

The present invention relates to a method and apparatus for treating obesity, and more specifically the invention relates to an artificial gastric valve that can be implanted in a patient for treating obesity.

2. Description of the Related Art

In the opinion of many health care experts, obesity is the largest health problem facing westernized societies and is considered an epidemic. From a medical standpoint, obesity is the primary risk factor for type 2 diabetes and obstructive sleep apnea. It increases the chances for heart disease, pulmonary disease, infertility, osteoarthritis, cholecystitis and several major cancers, including breast and colon. People with Body Mass Index ("BMI") greater than 40 are considered morbidly obese. People with BMI between 30 and 40 are considered obese. Most importantly, high BMI has been shown to cause a reduction in life expectancy.

From an economic standpoint, it is estimated that more than 100 billion dollars are spent on obesity and treating its major co-morbidities. This does not even consider the psychological and social costs of this epidemic problem. Despite these alarming facts, treatment options for obesity remain limited. The desire to eat and the body's counter regulatory system when caloric intake is reduced, makes the treatment of obesity quite a difficult task.

The obesity epidemic and its medical impact have been well documented. Currently over 50 billion dollars are spent on over the counter weight loss products and programs. The number of invasive surgical procedures such as gastric bypass and lap band being performed for severe obesity is rapidly increasing. In the past 5 years there has been a 450% increase in surgical procedures for obesity. On average these procedures cost more than $25,000. Furthermore, the complicated nature of these procedures and potential for negative long term effects make only the most obese candidates for these procedures. Despite the efficacy of current surgical procedures, there is a large opportunity to vastly improve their effectiveness and limit their complications. It is only in the last several years, that a majority of health care providers viewed obesity as a disease that justified invasive and aggressive management. The data for the negative impact of obesity on health is now overwhelming. Current procedures are merely first generation approaches and have not made an overall impact on obesity treatment and prevention. Consequently, there is a large market opportunity for medical devices that better understand the pathophysiology of obesity.

With over 60% of the United States Population obese or overweight, market size is limited only by the development of safe and effective technology. Currently, 150,000 bariatric cases are performed in the US. Approximately, 30,000 are lap bands. At present, staplers and medical devices for obesity are approximately a 500, million dollar market. This does not include the 50 billion dollars spent on weight loss products and programs. Nor does it include the estimated 100 billion dollar cost treating the complications of obesity. With the large discrepancy between need and effective treatments, most analysts believe that the obesity market could rival the cardiac stent market if proper devices are developed. The devices developed to date all have issues.

Gastric Bypass

Gastric Bypass is the most common surgical procedure performed to treat morbid obesity. The procedure involves using a stapler that cuts and divides tissue. This is used to produce a pouch that serves as a smaller stomach. This pouch is attached to a limb of divided intestine. Finally, intestinal continuity is restored by attaching the intestine to the intestine.

Numerous things happen when a gastric bypass is performed. The new stomach is smaller and holds less food. Food goes directly into the small intestine, bypassing the bottom portion of the stomach and the initial area of the intestine. Food does not mix with the digestive juices from the liver and pancreas until a large portion of the GI tract has been passed. As a result, the operation makes people eat less and causes impaired absorption of food, minerals and vitamins.

While effective, the bypass can cause numerous long term issues. There is a real mortality rate associated with the procedure. Poor iron absorption can cause anemia. Poor calcium absorption could cause osteopenia. Poor vitamin absorption can cause deficiency in Vitamin A, 0, or thiamine. Additionally, there is a risk of marginal ulcer, stricture, and other morbidity.

For these reasons, the number of patients seeking gastric bypass appears to have stabilized. For the last five years, growth has been exponential. Currently, patients are searching for the efficacy of bypass without the potential complications.

Besides the standard gastric bypass, there are other procedures that are similar. They include banded bypass, biliopancreatic diversion with duodenal switch and Scopinaro procedure. All combine some gastric alteration with an intestinal bypass. All offer weight loss. But all have a short and long term complication profile that preclude them from being considered ideal treatments.

Presently, all these procedures can be performed laparoscopically. While this offers faster recovery, reduced pain, and lower risk of hernia formation, it does not eliminate the short and long term complications associated with gastric bypass.

Laparoscopic Adjustable Gastric Banding

The purpose of the gastric band is to create a narrowing in the proximal stomach that functions as a valve. The valve reduces the space available for food in the stomach and delays the emptying of the stomach. This hopefully makes people eat less and want to eat less frequently. The band can be tightened with the insertion of liquid through a port that is placed beneath the skin. New generations will offer band inflation without an invasive needle stick. However, the outlet would still remain fixed and the band would still represent a high pressure zone.

The attraction of the band includes its low peri-operative morbidity and mortality. Since there is no alteration of the GI tract itself, recovery is rapid. However the fixed high pressure zone leads to numerous issues.

Certain patients never achieve an acceptable level of weight loss. When the band is tightened to enhance effect, there can be dilation of the pouch above the band and the esophagus. Patients complain of regurgitation and dysphagia. Also the high pressure that is transmitted proximally causes a stomach that is more resistant to distension and the forces caused by food bolus.

Several companies are expected to enter the LAGB market. Ethicon Inc, a division of Johnson and Johnson is expecting approval of there obtech band in 2007. Additionally they have accumulated IP that involves improved design including self adjustment. Other band companies in Europe include Mid-Band and Helioscope. A new entry is Endo-Art which offers an improved method of non invasive band adjustment.

Gastric Balloons

A simple concept to reduce food intake is the placement of a space occupying balloon. These are inserted with the help of an endoscope. The balloon is inflated to 600 to 850 cc. This occupies a large portion of space in the stomach and leads to early satiety.

There are numerous issues that have limited the clinical usefulness of balloons. The harsh acidic environment of the stomach can cause destruction of the balloon. As a result, the balloon needs to be replaced every six months. More importantly, the large balloon causes the stomach to reset. Since there is no external restriction the stomach can dilate. In fact the stomach can dilate to quite extreme levels. As the volume of a sphere changes with the radius to the third power, even a small level of dilatation can lead to an impressive increase in the size of the gastric reservoir.

As a result, most view balloons as a bridge for very high risk patients, to more efficacious treatment modalities, such as gastric bypass. Old version of the balloon such as the Taylor or Guerin balloons were recalled from the market. Bioenterics, the maker of the lap band has re-introduced the Bioenterics intragastric balloon, with their improved silicone.

Gastric Pacing

There are several investigational designs that have explored using electrical stimulation with the use of a pacemaker to either the gastric tract or essential nerves. The most investigated is trans gastric pacing utilized by Transneuronix, which was recently purchased by Medtronics, for a minimal value of 260 million dollars. With incentives, the deal could be worth one billion dollars.

This approach involves the insertion of electrical leads on the lesser curvature of the stomach, close to the fibers of the vagus nerve. These leads are attached to a pacemaker.

There are numerous theories regarding the effect of gastric pacing. The original hypothesis was that the pacing interfered with the normal electrical system of the stomach and caused a delay in gastric emptying. This delay would allow the stomach to stay full and reduce food ingestion. Unfortunately, gastric emptying studies failed to show consistent delay in gastric emptying. More recent theories involve stimulation of enteric nerves, and local hormonal factors.

Several large trials that have included sham arms have investigated the efficacy of gastric pacing. To date, they have not shown consistent efficacy. Recently, Medtronic announced that the most recent trial failed to demonstrate weight loss.

Another version using similar technology is being employed by Impulse Dynamics which is a privately held Israeli based. In their system, impedance is measured and the gastric pacing is linked to a change in impedance. Clinical trials are being done in Vienna and the USA.

Cyberonics Inc. has investigated the use of vagus nerve stimulation for obesity. Favorable animal data lead to a six patient clinical pilot. Results were similar to what was reported by Transneuronix. Two patients did well, two had limited efficacy and two had no effect at all. The conclusion was that there was a real effect, but that more investigation was needed to master the needed signal.

Leptos, a new start up is investigating the use of splanchnic nerve stimulation. Similar to the vagus nerve, the splanchnic nerve is a conduit for information from the stomach and intestines to the brain. Promising animal data has been generated and pilot human trials are planned. Leptos has completed a second round of financing at a valuation of 12 million dollars.

Perhaps the most futuristic approach is being developed by Intrapace. Their approach is to design an internally placed pacemaker that is inserted through a trans-oral approach. In addition to all the unknowns that the other stimulation products have, this approach adds new dimensions. They include the need for a small or rechargeable battery, limited space, the harsh gastric environment and the difficulty in generating the high power signal believed necessary to stimulate small C fibers.

All pacing concepts are based on stimulating the intrinsic wiring of the stomach and mimic what happens when the stomach is stimulated by the ingestion of food. The problem is that while we know that this wiring exists, we do not know the Morse code needed to decipher. The pacers generate an electrical signal that goes on or off. There is no crescendo or decrescendo response. Only Impulse Dynamics tries to overcome this obstacle. Additionally, there is no physiologic response to titrate the response. Thus only expensive clinical trials can be performed to see if the pacing is effective. The Transneuronix experience highlights these issues.

Many patients lost weight in their clinical trial. However, when compared to placebo the response was not statistically Significant. Other, than repeat an entire trial with different pacing parameters or a patient selection, there is little that can be done. Basically, improved parameters will need to be guessed and only a lengthy trial will determine whether effective.

Pacing strategies are attractive since they would be low risk procedures. However, they will be expensive and efficacy may prove difficult. Contrary to cardiac pacemakers, there is no short term way of determining whether you have achieved your clinical objective. As a result, improvements will be difficult to prove.

Other hurdles besides clinical approval, will be gaining reimbursement. These devices will be expensive and require battery change at regular intervals. Even if FDA requirements for pre-market approval are met, it will be a long time before reimbursement is obtained from a majority of commercial insurance plans. Furthermore, approval for Medicare reimbursement will be difficult. The expense of these devices and the cost of invasive implant and the need for battery change will reduce the number of potential self or cash pay recipients.

Endoscopic or Trans Oral Restriction or Sleeves

Trans-oral approaches offer the potential to have access to the GI tract without incision. Theoretically, procedures could be done in an outpatient setting without general anesthesia or endotracheal intubation. These approaches could limit morbidity and make the development of sepsis, wound breakdown and fistula less likely. Finally, the potential reduced cost of outpatient procedures could make treatment more affordable.

There is an extensive list of trans-oral approaches that are being developed. These include oral devices, bezoars that occupy space in the stomach, internal suturing devices, stents and grafts that serve as a conduit for food bypassing areas of caloric absorption, gastric clamping or fusion techniques, radiofrequency ablation and intra gastric pacing. At present, an oral device and a balloon that occupies space have been utilized in clinical practice. Endoscopic suturing has been done for gastric fistulas and dilated gastrojejunostomy attachments with promising early results. Suturing has also been done as a primary procedure for obesity in South America.

Oral Devices

The concept of an oral device is to occupy the space under the roof of the mouth. This forces patients to take smaller bites, eat slowly and hopefully eat smaller meals. The device, called the DDS, (Scientific Intake) is inserted by the patient prior to eating and removed at the conclusion of the meal. Each person has an impression produced and the device custom made. A recent modification allows for a chip to be inserted to check for compliance.

At present the device has been utilized by over 3000 people. There are no reports of any significant adverse events. An acute study performed at Pennington Institute revealed that the study group eat 23% less food and this was associated with a six pound weight loss. A multi-centered FDA trial was scheduled to begin in January of 2006, to objectively study the device and the compliance pattern of patients.

The future market of this device is not designed to be competitive with the companies products. This approached is being advocated as a first line and for those with minimal obesity. For success there will need to be compliance and extensive behavior modification will be combined with the oral device.

Internal Suturing and Gastric Clamping

Several approaches are being designed to reduced the size of the stomach and perform an internal restrictive obesity operation. The idea is to reduce gastric capacity similar to what is done with a vertical banded gastroplasty. Several established and startup companies are examining these techniques. They are attempting to utilize either a combination of a suturing device and methods that fuse the walls of the stomach.

Satiety Inc. a privately held start up, which has an approach to internally reduce the size of the gastric reservoir. They are developing tissue fusion and suturing device to accomplish this goal. There are several major issues. First there is the technical challenge of designing an endoscopic product that fits through a currently available endoscope or overtube to perform the procedure. Furthermore, if accomplished the durability of these procedures will have to be questioned. Staple breakdown rates of 10-20% have been reported for externally applied staplers. How internal sutures or fusion techniques will hold in the acidic gastric environment, remains to be determined. Furthermore, in open procedures, unless these procedures were reinforced with synthetic bands, they had very short term efficacy. Another major question will be the regulatory path and follow up period that the FDA will find acceptable. If more than one year of follow up is required, these durability issues may prove terminal.

Gastric Sleeves

Another technique to reproduce the benefits of a gastric bypass transorally are gastric sleeves or elephant trunks. The idea is to utilize a graft, that is anchored to the GI tract by an attachment device such as a stent. The graft would be lodged into the jejunum or proximal ileum. Food would travel down the conduit, not mixing with the digestive enzymes and reduce small bowel absorption. This could potentially be combined with a gastric restrictive device to imitate a gastric bypass. Others have also proposed combining such a technique with an Adjustable Laparoscopic Gastric Band.

Numerous start up companies that have raised capital at valuations approaching 20 million dollars, have taken this approach. They include GI Dynamics, Barosense and GastroRx.

Issues with sleeves or conduit procedures include, difficulty in fixation, potential for obstruction and kinking, migration and an unknown effect on food consumption. As food is in reduced contact with intestinal mucosa, this could actually stimulate recipients to eat more to compensate.

Insertion of foreign bodies into the gastro intestinal tract is different than placing stents into the vascular system. There are strong muscular contractions called peristalsis that drives food down the intestinal tract. These forces will make these devices difficult to anchor. Thus they will migrate and kink and cause intestinal obstruction. Additionally, the graft will serve as an absorber of the transient pressure increases seen with food consumption.

These devices will have to overcome all these technical barriers. Once these are overcome, then efficacy will need to be determined. These devices have no real precedent surgical procedure to predict their long term effectiveness and durability.

Most Common Techniques

The most common operation in the United States is the Gastric Bypass. With gastric bypass many investigators have reported weight loss results that exceed 70% of excess weight. However, this efficacy does not come without complication. The accepted mortality of the procedure is 1 in 200. Even higher figures have recently been reported among beneficiaries of Medicare. Furthermore, there is an increasing recidivism rate. Weight gain of 10 to 40% of maximum weight loss has been reported. Immediately after surgery, most patients report less desire to eat. Unfortunately, 6 to 12 months after surgery the urge to eat seems to return. Most, still cannot eat the portion size they once consumed. However they replace this with eating small amounts of calorically dense foods more often. There can be expansion of the pouch and dilation of the attachment between the stomach and the intestine.

Another view, is that the operation is fixed and unlikely to work better than immediately after it was performed. As the patient challenges the procedure, the tissue changes to allow more food to enter. The negative reinforcement the operation offers decreases over time. We learn what to eat, how to eat it and sub consciously learn tricks that allow us to return to the habits that made the patient obese.

Other common techniques include the lap band or adjustable gastric bands which have similar limitations. The band is a synthetic medical device that can be thought of as a ring that goes around the first portion of the stomach. Inside the ring is an inflatable balloon. This balloon can be tightened by inflating fluid that makes the outlet of the stomach smaller.

The purpose is to make the recipient eat less food and smaller portions. While the lap band is adjustable this does not change the fact that the restriction is fixed. The lap band creates a high pressure zone that delays food intake past this point. This high pressure is transmitted to all places above the band. This can lead to dysphagia, dilatation of the stomach and esophagus above the band, regurgitation and reflux. Furthermore, the persistent high pressure would make it more difficult for a limited bolus of food to initiate satiety signals. While early, research has shown that ghrelin (a hormone that has been linked to satiety) levels stay persistently high in lap band patients. Low ghrelin levels have been reported in post bypass patients and are thought to be partially responsible for the post operative anorexia experienced by patients.

The advantages of the lap band, compared to gastric bypass are multiple. The gastrointestinal tract does not have to be permanently altered. There is no malabsorption of vitamins and minerals. The operative morbidity and mortality is much lower. On the other hand, results are more variable. 10% of recipients have minimal weight loss. Secondary to poor weight loss or other symptoms caused by the fixed obstruction, the re-operative surgical rate is also approximately 10%.

As stated above, it is estimated that up to 60% of the population in the United States is obese or overweight. Of these patients, 5-6% are considered morbidly obese because they are approximately 50 kg above their ideal body weight. Treatment options include dietary modification, very low calorie liquid diet, pharmaceutical agents, counseling, exercise programs and surgery. Surgical procedures that restrict the size of the stomach and/or bypass parts of the intestine are the only remedies that provide lasting weight loss for the majority of morbidly obese individuals. Surgical procedures for morbid obesity are becoming more common based on long-term successful weight loss result. Increase awareness regarding the dangers of obesity combined with the fact that these procedures are now being done with a laparosope, in a minimally invasive manner, have made these procedures one of the fastest growing areas of surgery.

The surgeries which create malabsorption, such as the bypass operation, although effective in weight reduction, involve permanent modification of the GI tract and have a risk of short and long term complication and even death. A method to create restriction of food flow in the stomach involves a device called gastric band in which a band is tightened around part of the stomach. The band operation does not modify the GI tract at the time of surgery, however because the restrictive band is fixed in diameter, it can create long term complications. The fixed high pressure caused by the obstruction is transmitted to the gastro esophageal junction and esophagus. These structures are forced to accommodate this increased load. This can result in adaption of the pouch, esophageal dysfunction, and severe dysphagia. At present, only 50% of band recipients have what is considered a successful bariatric procedure. Annually 5% of patients require revision or band removal. Present day gastric bands are fixed in diameter with the ability to change the diameter via injection of liquid into a balloon. This type of diameter change involves a visit to the physician and is not dynamic. Thus people develop gastric pouch dilation, stoma obstruction, motility disturbances (pseudo achalasia), esophagitis and other symptoms related to a fixed barrier in the stomach.

This review of the obesity device field, emphasizes the need for a better surgical device for the treatment of obesity. The desired device would need to be easily placed. It would need to be reversible. It would need to make people eat less feel less hungry. It would need to be activated when it is needed, not be locked in the on position. It would need to be able to be altered to meet changing clinical needs.

SUMMARY OF THE INVENTION

The present invention relates to a device which automatically, is dynamically and progressively controls the stoma opening by using an Artificial Gastric Valve (nAGV") that is placed around part of the GI tract, preferably around the upper part of the stomach. The AGV can change its inside diameter on demand and thereby when the diameter of the AGV is reduced the stomach is compressed and a restriction of the flow of food in the stomach is created. Similarly, when the diameter is increased the stomach is relaxed to its natural state.

The change of diameter of the AGV which creates a change of diameter of the stomach and therefore restricts the flow of food occurs at times which are a function of start of food intake or other bodily actions taken by the patient consciously or unconsciously in relation to the start of eating. When the patient starts eating, a sensor senses one or more of the bodily actions that are taken immediately after start of eating such as for example receptive relaxation, esophageal relaxation near the GE junction as a result of a bolus of food going down to the stomach or the expansion of the stomach at the point where the AGV is located. The indication of start of eating causes the AGV diameter to reduce thereby constricting the stomach and restricting the flow of food. After eating, the AGV relaxes to its natural state and the stomach is relaxed back to its original condition. The range of variation in the inside diameter of the AGV can be from the natural diameter of the stomach down to a diameter of about 0.3 to 1 cm which amounts to almost a complete closure of the inside of the stomach. The device augments the natural body response to eating and creates a satiety feeling in addition to the main progressive restrictive effect which prevents the patient from excessive eating and causes weight loss without the side effects of a fixed diameter gastric band. The opening and closing of the AGV can be titrated to the individual patient by programming the software in an electronic controller. This will also have a block out feature, preventing too frequent activation and repetitive activation during the same time period. Additionally, the memory function will allow for the physician to understand how frequently the patient is eating.

The proposed system consists of an AGV padded on the inside to prevent erosion of the stomach tissue, a restrictive mechanism for reducing and increasing the inside diameter of the AGV, a sensor indicating start of eating and an electronic controller including an algorithm for automatically deciding on changing the diameter of the AGV, a power source based on a battery and possibly a remote charging system for charging a rechargeable battery. All of the parts are inserted laporascopically into the body. On the outside of the body it is possible to have a control unit for communicating with the controller 5 in the body in order to collect pertinent information and to modify the algorithm by reprogramming the software in the controller. In addition the part of the remote charging system and its energy supply are on the outside.

The proposed device being on demand, dynamically and progressively constricting the flow of food where most of the time the AGV is relaxed and the stomach is at its natural state, prevents major problems associated with constant restriction of gastric bands and therefore will prevent patients from additional operations and need to take out the implanted AGV. Problems associated with constant diameter gastric bands include gastric pouch dilation, stoma obstruction, motility disturbances such as pseudo achalasia, esophagitis and other symptoms related to a fixed barrier in the stomach. In addition, letting the stomach return to its natural state ensures a more natural feeling of satiety not affected by adaption of the stomach wall to fixed high pressure.

The present invention offers the combination of augmentation of satiety with the known effectiveness of gastric restriction. As the name suggests the approach is as logical and simple as ABC and has a far greater chance for long term success than the competition. The system is based on the lessons the founders have learned with open, laparoscopic and experimental pacing procedures. It is based on the understanding of the proximal gastro intestinal tract. As the device employ external restriction, it is believed that the path for regulatory approval and reimbursement will be more predictable than other start up firms in the obesity sector.

DETAILED DESCRIPTION OF THE PREFERRED EMBODIMENTS AND METHODS

The present invention relates to an Activated Bariatric Concept ("ABC") which is based on the insight gained by treating thousands of bariatric surgical patients and performing an equal number of procedures. Eating begins with the passage of a bolus of food into the esophagus. This bolus travels with the aid of peristaltic forces that are locally generated towards the stomach. At the junction of the esophagus and the stomach there exists a valve called the lower esophageal sphincter. This valve relaxes to allow food to enter. The stomach, which sits in a relaxed position, changes to allow food to enter. At the level of the fundus there is receptive relaxation. This means that the wall of the stomach relaxes to allow the food that is entering the stomach to cause a smaller increase in pressure.

Humans eat in a certain pattern. At first they eat rapidly. Then the pace slows as the stomach fills and the amount of distension and pressure on the stomach increases. These incremental forces create signals that travel from the stomach to the central nervous system and give the feeling of fullness and satiety. Past a certain point they may cause a feeling of bloating and discomfort. These gastric forces, are the bodies strongest satiety signals. This point is highlighted by the speed we begin our meals, followed by slower eating, until meal cessation.

The purpose of the present invention is to augment the natural response of the body. The object of the present invention is to sense the initiation of food consumption and provide alteration of the gastric tract that mimics what occurs when a person begins to eat. Thus at the origin of eating a powered device is activated that constricts one area of the stomach and allows expansion and distension of other areas. The result is to both physically restrict the amount of food that is eaten, as well as promote the satiety signals that are produced when distension or increased pressure in the gastric lumen occurs. This unique approach also times the signals to coincide to the period when the body is most receptive.

The preferred embodiment of the present invention includes an externally placed gastric constrictor that is attached to a power source and sensing arm. As the constrictor tightens, the area above will distend and a smaller amount of food will cause a transient rise in pressure in the proximal stomach. The purpose is to augment what occurs in the rapid eating period. Furthermore the proximally placed constricting ring or valve will limit the reservoir available for food intake. This system will combine gastric restriction, and augment satiety.

Figure 1A:
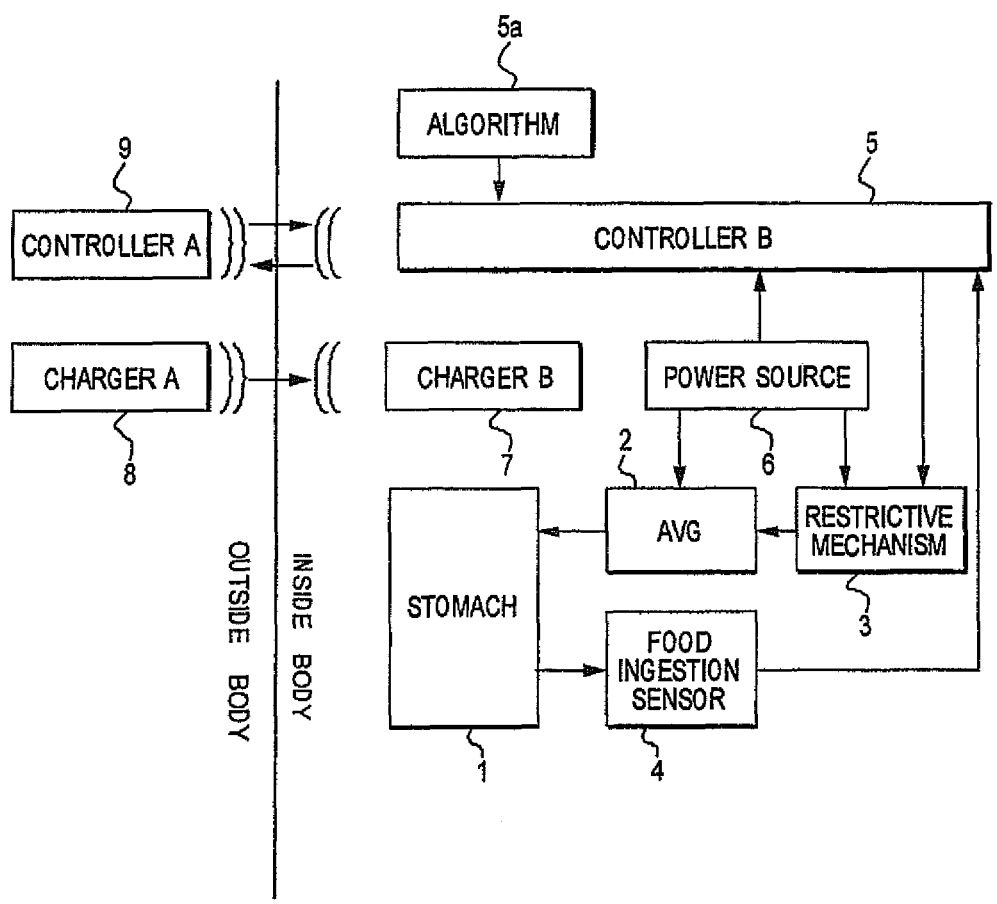
FIG. 1a is a block diagram of the AGV of the present invention.
Figure 1B:
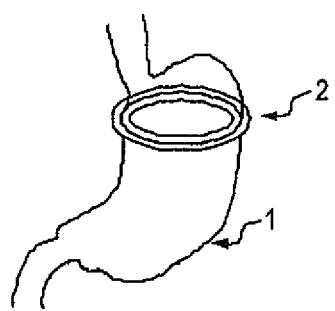
FIG. 1b is an illustration of the AGV positioned with respect to the stomach.
Figure 1C:
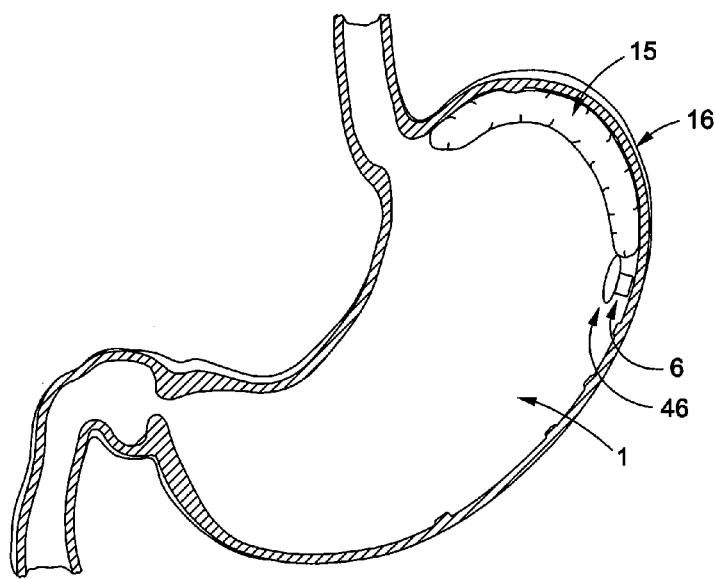
FIG. 1c is an illustration of an intra luminal device located inside the stomach in a non-dilated state.
Figure 1D:
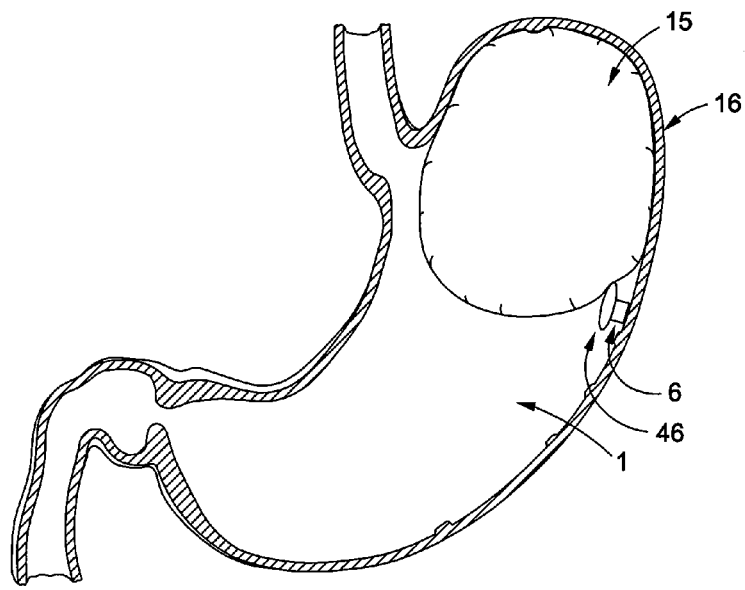
FIG. 1d is an illustration of an intra luminal device located inside the stomach in a dilated state.

A further modification, for example as shown in FIG. 1c, could include a trans orally placed internal system or device 15 that will be lodged into the lumen of the stomach 1. This system or device 15 will be anchored to the gastric wall 16 and dilate when stimulated, for example as shown in FIG. 1d, occupying space and stretching the gastric wall 16. Contrary to balloons, this system will exist in the relaxed position, thus preventing gastric accommodation.

The purpose of the present invention is to place an artificial valve on the stomach and preferably at a much higher level of the stomach than is conventional in the art. The valve begins to tighten when wet swallowing or eating commences. This provides progressive gastric restriction, limits food intake and promotes early satiety. The valve gradually loosens providing controlled emptying of the stomach and causing reduced hunger. The dynamic nature of the valve will prevent long term motility and esophageal dilation.

The present invention includes a device that augments the natural response of the body to eating and reduces food intake. The device is preferably referred to as an Artificial Gastric Valve (UAGV") based on progressive physical restriction of part of the gastrointestinal (GI) tract, preferably the stomach, with the restriction being controlled by the initiation of food intake. During periods when food is not being ingested, the device is left in the relaxed position. Thus permanent derangements in esophageal and stomach anatomy and function would not be expected.

Referring now to FIG. 1 a, a block diagram illustrates the device, and it is divided into portions that are either inside the body or that are outside the body. The method of operation is hereby described according to FIG. 1a. An AGV 2 made of semi rigid material or thin metal strip, is disposed around the upper part of the stomach 1 in perpendicular to the vertical disposition of the stomach 1 so that the inside diameter of the AGV 2 is in contact with the outer part of the stomach 1 at the position where the AGV 2 is encircling the stomach.

A preferred position of the AGV is shown in FIG. 1b. Initially the AGV is open wide enough so that it does not exert pressure on the stomach and therefore does not create a restriction on the flow of food through the stomach. Attached to the AGV 2 is a two directional restrictive mechanism 3. The restrictive mechanism 3 is capable of constricting the AGV 2 as well as relaxing to it. The restrictive mechanism 3 is capable of progressively reducing the inside diameter of the AGV 2, creating a pressure on the stomach so that the diameter of the stomach is reduced and the flow of food through the stomach is restricted. A sensor 4 is capable of sensing the bodily reactions to the start of food ingestion and to send a signal indicating start of eating to a controller B 5.

The controller B 5, using an algorithm 5a, upon receiving the signal of start of eating from the sensor 4, sends a signal to the restrictive mechanism 3 to operate, reduce the diameter of the AGV 2 and create a restriction on food flow. As a result the patient is prevented from eating excessively. After the patient stops eating, the controller B 5 sends a signal to the restrictive mechanism to relax and allows the stomach 1 to get back to its original diameter and natural state. The controller B 5 is using the algorithm 5a to decide on the time between start of eating and close of the AGV 2, the rate of closing the AGV 2 and the extent to which the AGV 2 is closed. Similarly the controller B 5 decides on how long after start of eating the AGV 2 opens, at what rate of opening and to what extent. It is also possible for the sensor to indicate stop of eating for use in deciding when to open the AGV 2 and to what extent. The algorithm 5a can be designed and individually adapted to the patient based on his or her eating habits and anatomy. The algorithm 5a can be modified from outside the body by wireless signals from controller A 9 disposed outside the body to controller B 5 inside the body. Also, controller A 9 can receive information from controller B 5 via bi-directional wireless communication to allow the physician to collect data and information on the times of operation of the restrictive mechanism 3. The physician can modify the algorithm 5a to allow the patient more or less freedom to eat by changing the time at which the restrictive mechanism 3 starts to operate after the patient starts to eat, the rate of opening, the extent of opening and the time the mechanism 3 relaxes the AGV 2, the rate of relaxation and the extent of relaxation. The controller B 5, restrictive mechanism 3 and sensor 4 for start of eating receive electrical power from a power source such as a battery or power source 6. If needed, such battery can be charged using a remote charger A 8 which inductively transmits energy to charger B 7 for charging such battery.

Figure 8:
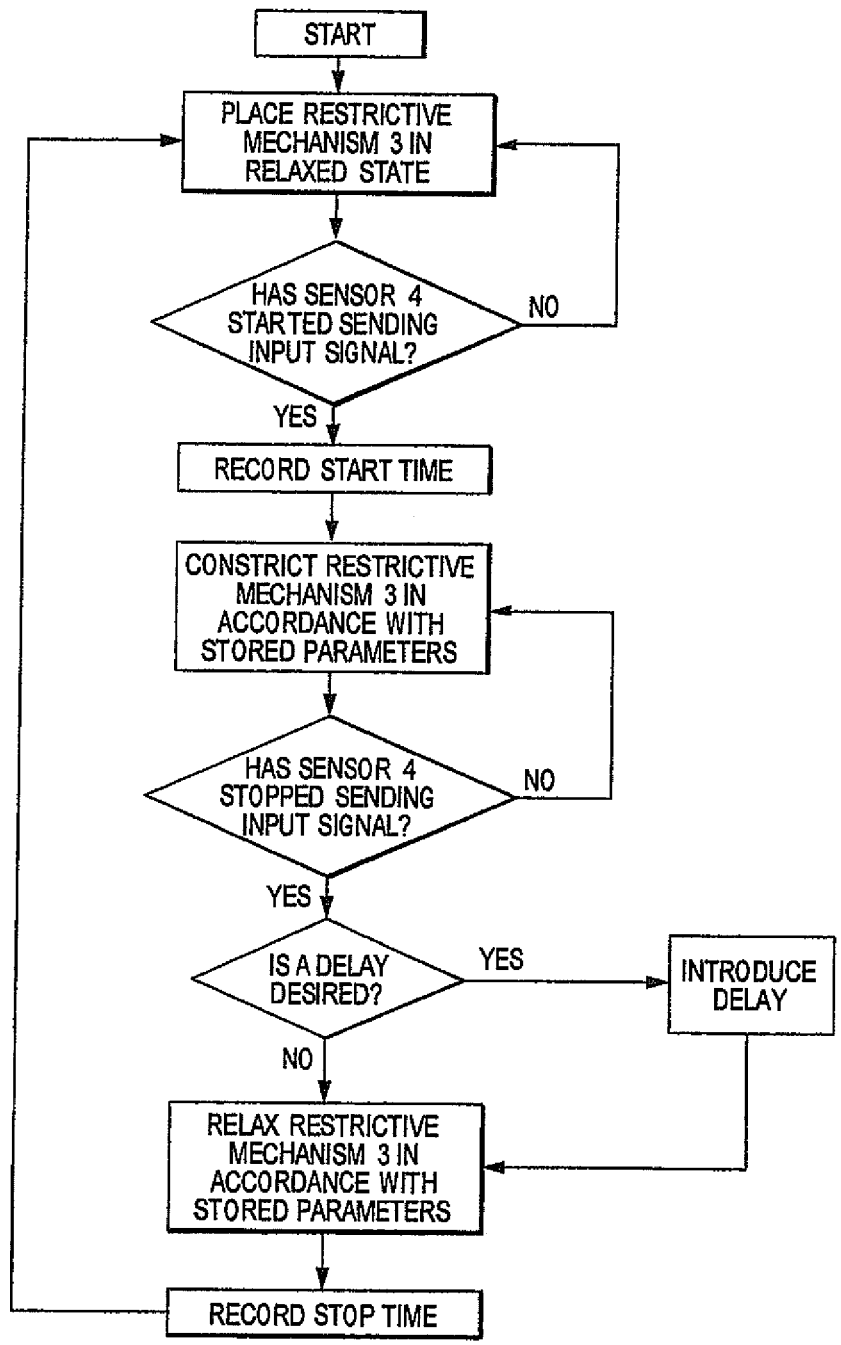
FIG. 8 is a flow chart of a first control algorithm.
Figure 9:
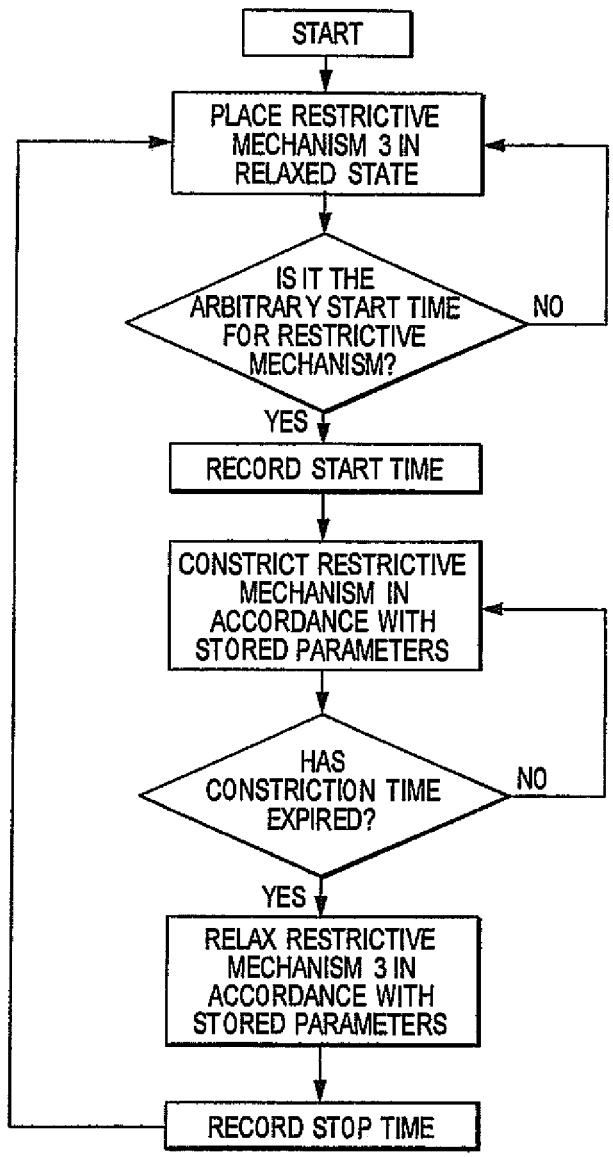
FIG. 9 is a flow chart of a second control algorithm.
Figure 10:
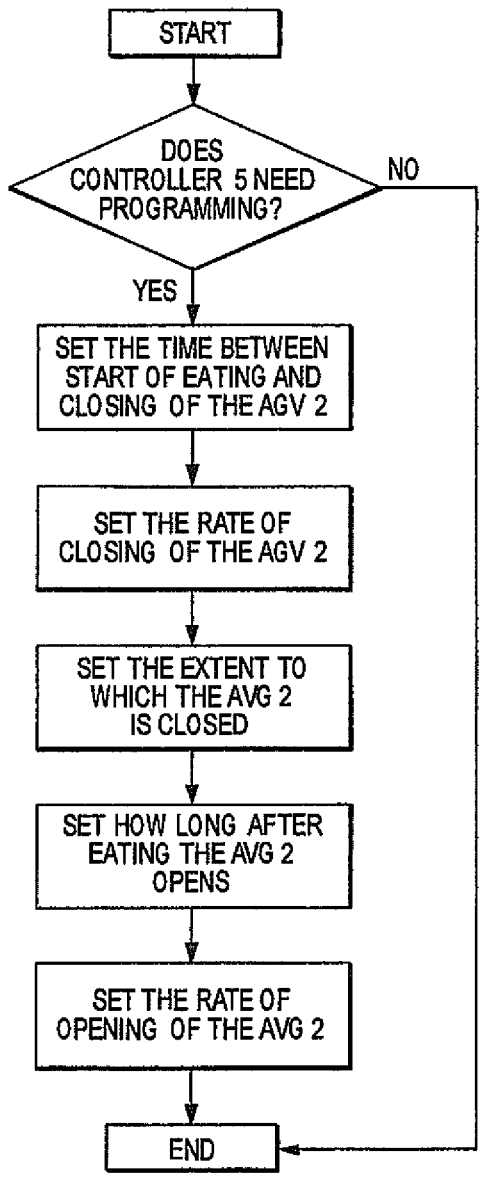
FIG. 10 is a flow chart of a subroutine for programming the controller of the present invention.

The algorithm 5a preferably includes at least two embodiments as illustrated in the flow charts of FIGS. 8 and 9. In the embodiment of FIG. 8, the algorithm 5a controls the AGV 2 in accordance with an input signal from a sensor 4. When there is an input signal from the sensor 4, the AGV 2 is constricted in accordance with stored parameters and the timing of the constriction is stored in the memory of either controllers 5, 9. The relaxation of the AGV 2 is also controlled in accordance with the input signal from the sensor 4 and stored parameters. In the embodiment of FIG. 9, the algorithm 5a controls the AGV 2 in accordance with arbitrary times that are programmed into the controllers 5, 9. These arbitrary or predetermined times correspond to time periods when food is expected to be ingested. When the arbitrary time occurs, the AGV 2 is constricted in accordance with stored parameters and the timing of the constriction is stored in the memory of either controllers 5, 9. The relaxation of the AGV 2 is also controlled in accordance with arbitrary times and stored parameters. If desired the relaxation of the AGV 2 may be delayed by a predetermined time period determined by a physician. The stored parameter are programmed into the controllers 5, 9 in accordance with the subroutine illustrated in the flow chart of FIG. 10. It is also possible that the AGV 2 may be constricted and relaxed in accordance with input from the sensor 4 and at arbitrary or predetermined times programmed into the controllers 5,9.

Figure 2A:
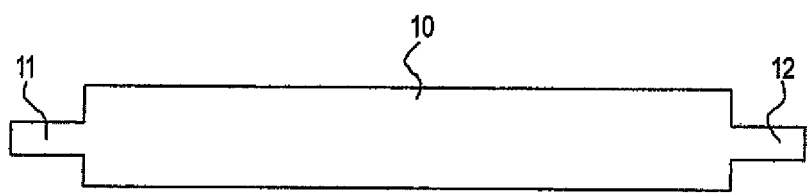
FIG. 2a is a schematic top view of the AGV.
Figure 2B:
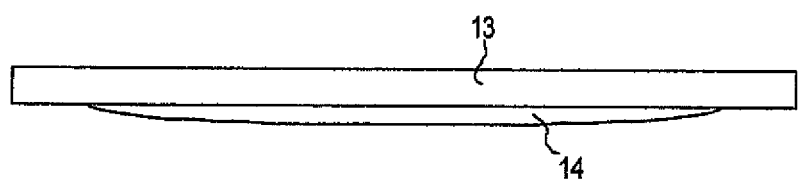
FIG. 2b is a schematic side view of the AGV.

The AGV 2 without the restrictive device 3 is shown in FIG. 2a and FIG. 2b. The AGV 2 is originally made of a long strip 10 shown in a top view having a predetermined length and width, made of semi rigid material, with ends 11 and 12 that connect to each other. The connection of the two ends could be with a buckle or a snap-on or other method to form a closed loop for embodiments in which the outer diameter of the AGV stays constant, or could be of a different type connection, such as connecting directly to a motor for other embodiments in which the outside diameter of the AGV changes during operation of the AGV. The length and width of strip 10 are approximately 10 cm and 1-5 cm respectively. A side view of side 13 of the AGV 2 is shown in FIG. 2b. The inside of the strip 10 is padded with a cushioning material 14 that prevents erosion of the stomach tissue as a result of restricting and relaxing the stomach by the AGV 2. The material can be soft material in one preferred embodiment and could be a balloon filled with liquid or gas in other embodiments. The balloon could be sealed, or could be connected to a source of liquid or gas and a restrictive mechanism inflates or deflates said balloon on demand.

The AGV 2 is inserted into the body laporascopically, disposed around the stomach and the two ends of the strip 10 are connected together to create a closed loop, leaving the soft cushioning portion 14 in contact with the stomach tissue.

The sensor 4 for start of eating relies on a known clinical fact that the process of start of eating is responsible for a series of bodily actions such as receptive relaxation of the stomach, saliva secretion, chewing, swallowing, secretion of hormones, change in blood glucose level, change in heart rate variability, expansion of the stomach and more. The sensor 4 for start of eating senses one or more of such bodily actions. In one preferred embodiment the receptive relaxation of the stomach can be sensed by strain gauges attached to the outside of the stomach or by sensing the electrical signals associated with receptive relaxation. Such signals can be measured with electrodes attached to the outside wall of the stomach or by electromagnetic sensors in a way similar to the method of cutaneous Electro Gastro-Graphy (EGG). The electromagnetic sensing can be done inside the body, or can be done cutaneously and the results can be transmitted to controller A 9.

Figure 7:
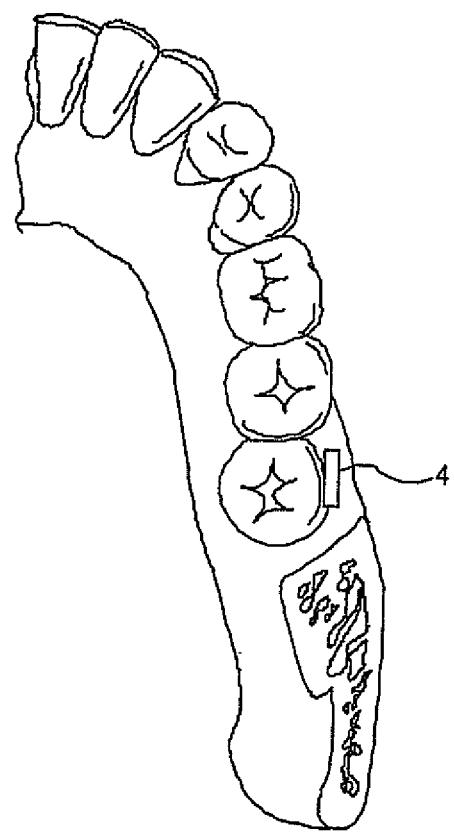
FIG. 7 is a drawing of a sensor disposed on a tooth.

Since the purpose of the artificial gastric valve 2 is to turn on the system at the initiation of food ingestion, it is preferable to utilize a sensing mechanism that determines that a person has started to swallow food or liquids. As shown in FIG. 7, the sensor 4 can be placed in the oral cavity and be designed to detect the pressure of mastication or other oral signal. The sensor can also be placed at the level of the esophagus and can be internally placed by endoscopy to sit on the mucosa. Alternatively, the sensor 4 can be placed around the GE junction and detect pressure change, motion, or expansion of this area with the passage of a bolus of food. The sensor 4 could be placed anyplace within or external to the GI tract, with the purpose of activating a system that either constricts or distends the stomach.

The sensor signal can include an ultrasound, infrared, electrical, radio frequency, magnetic, motion signal, that is directed at the lumen of the stomach or esophagus and initiates the process. For example as food goes through the lumen of the GI tract a signal is sent, and when this is absorbed, deflected or altered by food or luminal contents activates the system. Similarly a reflector could be placed opposite the signal and whenever the reflector is blocked the system is activated. The sensor can be current and voltage measurements on the stomach to measure parameters such as stomach impedance which correlates with start of eating.

The sensor could be a infrared beam that is combined with spectroscopy to detect a change in tissue perfusion, such as an increase in oxygen saturation which correlates to increased arterial blood flow to the stomach when food arrives at the stomach and it is active.

The sensor could be other measure of increased blood flow to the stomach or other signal such as temperature change, change in local chemistry, which detect a subtle change in local environment.

The sensor 4 could also be placed in the arm or in a combination of places and detect a motion or action that is consistent with bringing food toward the GI tract. The sensor 4 could detect changes in saliva or other GI tract secretion that is produced with the onset of eating.

Once activated, the system can be placed on and constrict the stomach at a steady rate controlled manner to a predetermined level. Alternatively, the sensor 4 can serve as a gradient and each time the system detects food the constrictor is tightened or an internal system, like the examples shown in FIGS. 1c-d, is inflated progressively.

The system controller is equipped with a memory. The purpose is to determine the number of times the system is activated. This information can be used to change speed of constriction or inflation, provide information for clinicians and alter the rate of emptying or any of the parameters of the system. The memory can also store dietary information related to the output of sensor 4 or other sensors, for example a blood sugar sensor, that are coupled to the internal controller 5. The memory can function as an internal data base of information and data that can be extracted by a physician utilizing the external controller 9.

Figure 3:
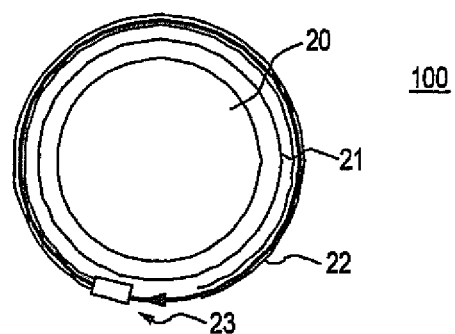
FIG. 3 is an illustration of a mechanical embodiment of the present invention.

In a preferred embodiment 100 the mechanism for progressive restriction of the stomach is mechanical in nature and acts directly on the AGV to tighten it or release it. Such mechanical action can be done for example by pulling one side of the strip 10 around the other part or inside the other part by use of a small motor as shown in FIG. 3. In FIG. 3 the stomach cross section is indicated by 20, the cushioning 21 can be a soft material or a sealed balloon. A small motor 23 acts on the AGV 22 to reduce its diameter by pulling or releasing one end of the AGV in relation to the other end of the AGV.

Figure 4:
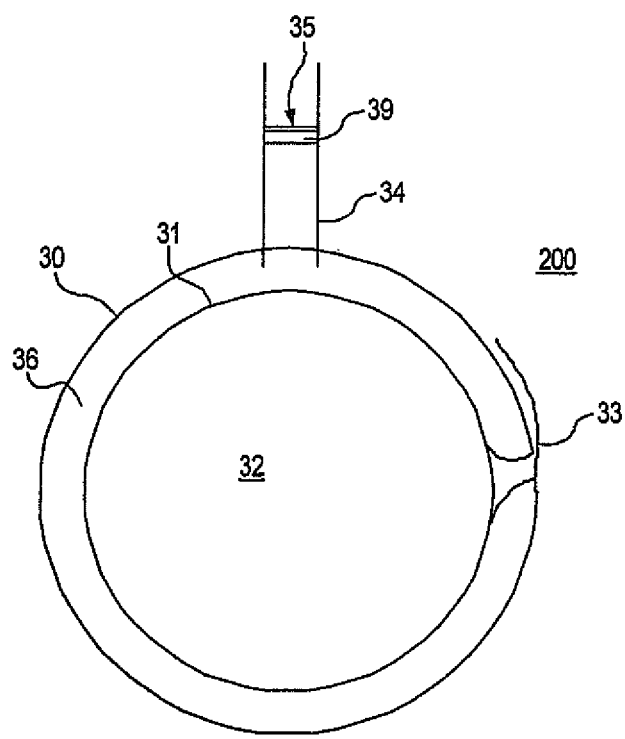
FIG. 4 is an illustration of a embodiment of the present invention that includes a piston.

In another preferred embodiment 200 described in FIG. 4, the AGV itself does not change in dimensions, only a balloon 36 on the inside of the AGV is changes its volume and pressure. In FIG. 4 the stomach cross section is indicated by 32, the AGV is indicated by 30 with 33 being the connection of the two ends of the AGV. A balloon 36 is connected to a tube 34 having a piston 39 and a mechanism to push liquid through the tube and into said balloon 36. The inside 31 of the balloon 36 pushes against the stomach 32. The borders of the balloon are indicated by 31 on the inside and 30 on the outside. The balloon 36 connects to the tube 34 and a piston, and the balloon 36 and the tube 34 are filled with a liquid such as saline solution. A motor 35 acts on the piston and thereby increases or decreases the pressure in the balloon 36 and therefore increases or decreases the diameter of the AGV on demand in a progressive manner. In another embodiment the pushing can be done by compressing a bellow filled with liquid.

Figure 5:
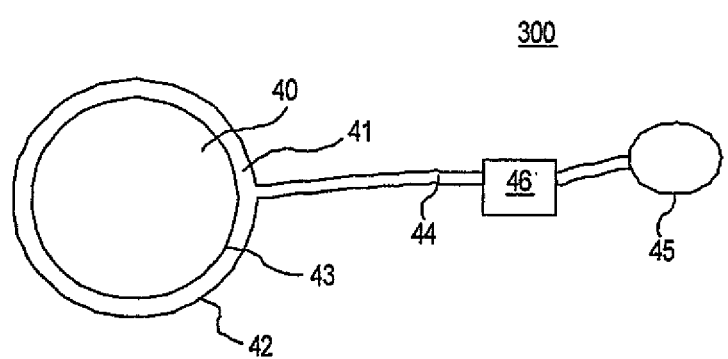
FIG. 5 is an embodiment of the present invention that includes a liquid reservoir and pump.
Figure 6:
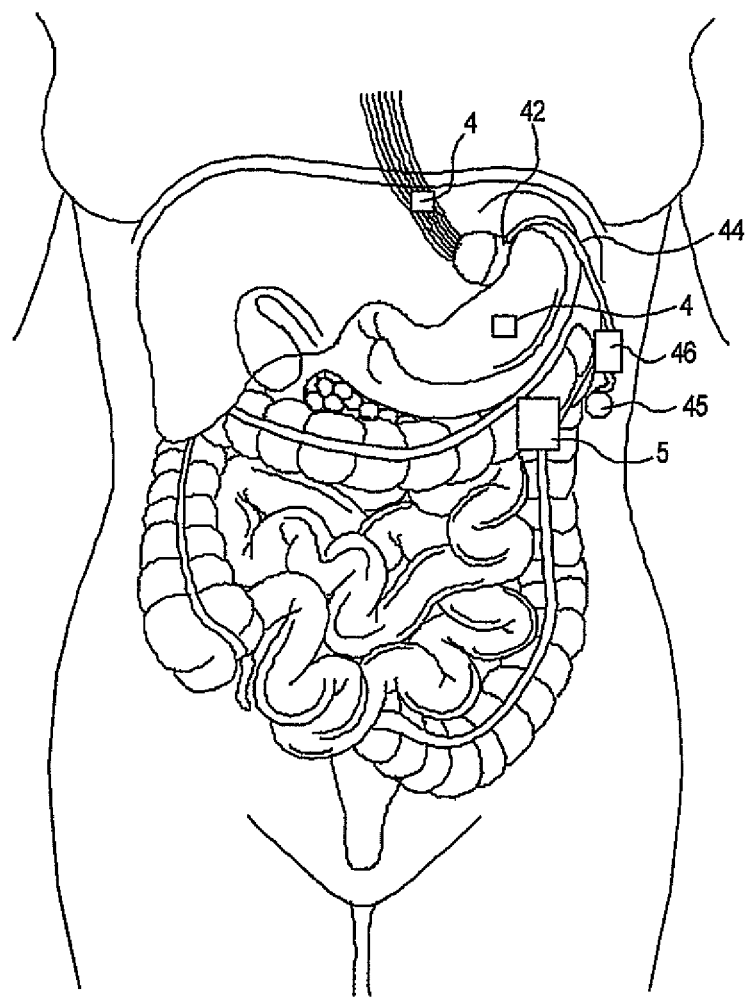
FIG. 6 is a drawing of the present invention disposed within the human body.

In yet another embodiment 300 of the restrictive mechanism shown in FIG. 5, the stomach 41 is encircled with an AGV 42 and a balloon 43 similarly to embodiment 200. The balloon 43 is filled with liquid, such as saline solution, and is connected via a tube 44 to a reservoir 45 and a pump 46. The pump, controlled by the controller B 5, can pump the liquid into the balloon and out of the balloon and increase or decrease the diameter of the stomach 41 to create a progressive restriction on the flow of food and relaxation of the stomach when the patient is not eating.

The system can be designed as a ring, helix or blanket. It could have compartments that are activated at different or the same time. The system could also be placed internally, for example the embodiment shown in FIG. 1*c*, as a bezoar 15 into the stomach 1 and anchored by an attachment to the gastric wall 16. Food would hit the sensor which would cause the inflation of the bezoar 15 causing gastric distension.

Similar to all the above, rate of inflation and deflation could be altered based on feedback of the system or device history.

What is claimed is:

1. A method for treating an overweight patient, comprising:
    endoscopically placing a dilating intra luminal device in a non-dilated state inside a stomach of the patient; and
    placing a sensor and a controller inside the patient's body, the sensor configured to sense initiation of eating,
    the controller configured to automatically control, using a control algorithm and responsive to the initiation of eating, an extent of dilation of the intra luminal device and wirelessly transmit to outside the body of the patient information related to the sensing initiation of eating or the controlling the extent of dilation of the intra luminal device, the controller configured to move the intra luminal device from a non-dilated state to a dilated state at a speed, the speed being variable, the controller deciding the speed based on the control algorithm.

2. The method of claim 1, wherein the control algorithm is configurable from outside the body of the patient via wireless transmission.

3. The method of claim 1, wherein movement of the intra luminal device from the non-dilated state to the dilated state is initiated by the start of eating or other bodily functions related to eating.

4. The method of claim 1, wherein movement of the intra luminal device from the non-dilated state to the dilated state is initiated by a food hitting the intra luminal device.

5. The method of claim 1, wherein the sensor is configured to sense cessation of eating and the controller is configured to control the extent of dilation of the intra luminal device after the cessation of eating.

6. The method of claim 5, wherein the controller is configured to determine whether a delay should be introduced after the sensing cessation of eating and before the controlling the extent of dilation of the intra luminal device and introducing the delay when so determined.

7. The method of claim 1, wherein the controller is configured to store a plurality of event times associated with the controlling the extent of dilation of the intra luminal device including initiation of eating, cessation of eating, dilation of the intra luminal device and non-dilation of the intra luminal device.

8. The method of claim 1, wherein the controller is configured to decide a speed of non-dilation for the intra luminal device.

9. The method of claim 8, wherein the speed that the controller moves the intraluminal device from the non-dilated state to the dilated state and the speed of non-dilation can be altered by the controller based upon feedback.

10. The method of claim 1, wherein the control algorithm is customized for the particular patient.

11. An apparatus for treating an overweight patient, comprising:
    a dilating intra luminal device that is adapted to be endoscopically disposed inside a stomach;
    a sensor for sensing initiation of eating; and
    a controller, using a control algorithm and responsive to the sensor, for automatically controlling an extent of dilation of the intra luminal device and configured to wirelessly transmit to outside the body of the patient information related to the sensing initiation of eating or the controlling the extent of dilation of the intra luminal device, the controller configured to move the intra luminal device from a non-dilated state to a dilated state at a speed, the speed being variable, the controller deciding the speed based on the control algorithm.

12. The apparatus of claim 11, wherein the control algorithm is configurable from outside the body of the patient via wireless transmission.

13. The apparatus of claim 11, wherein movement of the intra luminal device from the non-dilated state to the dilated state is initiated by the start of eating or other bodily function related to eating.

14. The method of claim 11, wherein movement of the intra luminal device from the non-dilated state to the dilated state is initiated by a food hitting the intra luminal device.

15. The apparatus of claim 11, wherein the sensor is adapted for placement in the mouth of the patient.

16. The apparatus of claim 11, wherein the sensor is adapted for placement on an extremity of the patient.

17. The apparatus of claim 11, wherein the sensor is adapted for placement on the gastrointestinal tract of the patient.

18. The apparatus of claim 11, wherein the sensor is responsive to bodily actions selected from the group comprising receptive relaxation of the stomach, saliva secretion, chewing, swallowing, secretion of hormones, changes in blood glucose level, changes in heart rate variability or expansion of the stomach, or changes in electrical parameters of the stomach, including impedance.

19. The apparatus of claim 11, wherein the sensor is responsive to energy selected from the group comprising ultrasound, infrared, electrical, radio frequency, or magnetic.

20. The apparatus of claim 11, wherein the sensor is responsive to a measure of increased blood flow to the stomach, temperature change, change in local chemistry, or change in local environment.

21. The apparatus of claim 11, further comprising a memory for storing information related to operation of the intra luminal device.

22. The apparatus of claim 21, wherein the information includes dietary information.

23. The apparatus of claim 21, wherein the information includes blood sugar measurements.

24. The apparatus of claim 11, wherein the sensor is configured to sense cessation of eating and the controller is configured to control the extent of dilation of the intra luminal device in response to the sensing of cessation of eating.

25. The apparatus of claim 24, wherein the controller is configured to determine whether a delay should be introduced after cessation of eating and before the controlling the extent of dilation of the intra luminal device and introducing the delay when so determined.

26. The apparatus of claim 11, wherein the controller is configured to store a plurality of event times associated with the controlling the extent of dilation of the intra luminal device including initiation of eating, cessation of eating, dilation of the intra luminal device and non-dilation of the intra luminal device.

27. The apparatus of claim 11, wherein the controller is configured to decide a speed of non-dilation for the intra luminal device.

28. The apparatus of claim 27, wherein the controller is configured to alter the speed that the controller moves the intraluminal device from the non-dilated state to the dilated state, and the speed of non-dilation based upon feedback.

29. The apparatus of claim 11, wherein the control algorithm is customized for the particular patient.

* * * * *